US005833891A

United States Patent [19]
Subramaniam et al.

[11] Patent Number: 5,833,891
[45] Date of Patent: Nov. 10, 1998

[54] METHODS FOR A PARTICLE PRECIPITATION AND COATING USING NEAR-CRITICAL AND SUPERCRITICAL ANTISOLVENTS

[75] Inventors: Bala Subramaniam, Lawrence, Kans.; Said Saim, New Milford, Conn.; Roger A. Rajewski; Valentino Stella, both of Lawrence, Kans.

[73] Assignee: The University of Kansas, Lawrence, Kans.

[21] Appl. No.: 805,215

[22] Filed: Feb. 27, 1997

Related U.S. Application Data

[63] Continuation-in-part of Ser. No. 723,463, Oct. 9, 1996.

[60] Provisional application No. 60/012,593 Mar. 1, 1996 and provisional application No. 60/012,592 Mar. 1, 1996.

[51] Int. Cl. $^6$ .............................. B01B 11/00; B01J 2/04; B05D 1/02

[52] U.S. Cl. .................................. 264/7; 264/12; 264/13; 264/14; 427/213
[58] Field of Search .................................. 264/7, 12, 13, 264/14; 427/213

[56] References Cited

U.S. PATENT DOCUMENTS

| | | | |
|---|---|---|---|
| 4,900,558 | 2/1990 | Barry et al. . | |
| 5,043,280 | 8/1991 | Fischer et al. . | |
| 5,301,664 | 4/1994 | Sievers et al. . | |
| 5,308,648 | 5/1994 | Prince et al. . | |
| 5,344,676 | 9/1994 | Kim et al. ................................ | 427/468 |
| 5,360,478 | 11/1994 | Kurkonis et al. . | |
| 5,389,263 | 2/1995 | Gallagher ................................ | 210/729 |

FOREIGN PATENT DOCUMENTS

| | | |
|---|---|---|
| 0542314 | 5/1993 | European Pat. Off. . |
| 9201446 | 2/1992 | WIPO . |
| 9501221 | 1/1995 | WIPO . |
| 9501324 | 1/1995 | WIPO . |

OTHER PUBLICATIONS

Wilcox et al.; Liquid Atomization in a High Intensity Sound Field; A.I.Ch.E. Journal; vol. 11, No. 1, pp. 69–72 (1965).

Lefebvre; Arthur H.; Atomization and Sprays; pp. 136–153 (1989).

Heat Systems Ultrasonics, Inc. Brochure, Sonimist Ultrasonic Spray Nozzles.

(List continued on next page.)

*Primary Examiner*—Mary Lynn Theisen
*Attorney, Agent, or Firm*—Hovey, Williams, Timmons & Collins

[57] ABSTRACT

Improved methods and apparatus for particle precipitation and coating using near- or supercritical fluid conditions are described. A fluid dispersion having a continuous phase dispersant and at least one precipitatable substance therein is contacted with a supercritical fluid (SCF) antisolvent so as to generate focused high frequency antisolvent sonic waves, breaking up the dispersion into extremely small droplets; the enhanced mass transfer rates between the droplets and the antisolvent causes precipitation of very small particles on the order of 0.1–10 $\mu$m. In coating processes, a turbulent fluidized flow of core particles is created using an SCF antisolvent in an enclosed zone. The core particles are contacted therein at near- or supercritical conditions by a fluid dispersion containing a dispersant together with a precipitatable substance. The antisolvent depletes the dispersant and the substance is precipitated onto the fluidized core particles. In another aspect of the invention, a process for preparing and administering a medicament using only a single container is provided. In such method, a fluid dispersion having a dispersant with the medicament therein is contacted with an antisolvent at near- or supercritical conditions within a use container, so as to directly precipitate small particles of the medicament in the container. The antisolvent is then removed and the use container is sealed with the medicament particles therein. Thereafter, dose(s) of the medicament can be withdrawn from the use container and administered to a patient.

57 Claims, 14 Drawing Sheets

OTHER PUBLICATIONS

York et al.; Particle Engineering by Supercritical Fluid Technologies for Powder Inhalation Drug Delivery; Respiratory Drug Delivery V, 1996, pp. 231–239.

Yeo et al.; Supercritical Antisolvent Process for Substituted Para–linked Aromatic Polyamides: Phase Equilibrium and Morphology Study; Macromolecules 1993; 26, 6207–6210.

Yeo et al.; Formation of Microparticulate Protein Powders Using a Supercritical Fluid Antisolvent; Biotechnology and Bioengineering, vol. 41, pp. 341–346 (1993).

Dixon et al.; Polymeric Materials Formed by Precipitation with a Compressed Fluid Antisolvent; AIChE Journal, Jan. 1993, vol. 39, No. 1, pp. 127–139.

Tom et al.; Formation of Bioerodible Polymeric Microspheres and Microparticles by Rapid Expansion of Supercritical Solutions; Biotechnol. Prog. 1991, 7, 403–411.

Bodmeier et al.; Polymeric Microspheres Prepared by Spraying into Compressed Carbon Dioxide; Pharmaceutical Research, vol. 12, No. 8, 1995.

Niwa et al.; Preparations of Biodegradable Nanospheres of Water–soluble and Insoluble Drugs with D, L–lactide/glycolide Copolymer by a Novel Spontaneous Emulsification Solvent Diffusion Method, and the Drug Release Behavior, Journal of Controlled Release, 25 (1993) 89–98.

Sanchez et al.; Development of Biodegradable Microspheres and Nanospheres for the Controlled Release of Cyclosporin A; International Journal of Pharmaceutics, 99 (1993) 263–273.

Dixon, Microcelluar Microspheres and Microballons by Precipitation With a Vapour–liquid Compressed Fluid Antisolvent; Polymer, vol. 35, No. 18 (1994).

Dixon et al; Formation of Microporous Polymer Fibers and Oriented Fibrils by Precipitation with a Compressed Fluid Antisolvent; J. Applied Polymer Science, vol. 50, 1929–1942 (1993).

Randolph et al.; Sub–Micrometer–Sized Biodegradable Particles of Poly(L–Lactic Acid) via the Gas Antisolvent Spray Precipitation Process; Biotechnol. Prog. 1993, vol. 9, No. 4.

DeBenedetti; Supercritical Fluids as Particle Formation Media; NATO ASI Series, E: Applied Sciences, vol. 273 (1994).

Yeo et al. Secondary Structure Characterization of Microparticulate Insulin Powders; J. Pharmaceutical Sciences, vol. 83, No. 12, Dec. 1994.

METHODS FOR A PARTICLE PRECIPITATION AND COATING USING NEAR-CRITICAL AND SUPERCRITICAL ANTISOLVENTS

CROSS REFERENCE TO RELATED APPLICATIONS

The benefit of the following Provisional Patent Applications are claimed: Ser. No. 60/012,593, filed Mar. 1, 1996, and entitled RECRYSTALLIZATION OF NANOPARTICLES OF SUBSTANCES SOLUBLE IN AN ORGANIC SOLVENT; AND COATING OF MICROPARTICLES INSOLUBLE IN AN ORGANIC SOLVENT WITH A SUBSTANCE SOLUBLE IN THE SAME ORGANIC SOLVENT, and Ser. No. 60/012,592, filed Mar. 1, 1996 entitled PRODUCTION OF PHARMACEUTICAL DRUG PRODUCTS BY LYOPHOBIC PRECIPITATION USING NEAR- AND SUPERCRITICAL FLUIDS. This is also a continuation-in-part of application Ser. No. 08/723,463, filed Oct. 9, 1996.

FIELD OF THE INVENTION

The present invention relates to a method and an apparatus for extremely small particle precipitation, wherein a fluid dispersion containing a substance to be precipitated is contacted with a supercritical fluid (SCF) antisolvent such as carbon dioxide under near-or supercritical temperature and pressure conditions for maximizing small particle formation. The invention provides spray techniques wherein the interphase mass transfer rate is maximized between small droplets of the dispersion and antisolvent so as to generate precipitated particles having an average diameter of from about 0.1–10 μm. The invention also includes supercritical fluid coating techniques wherein fluidized core particles are coated with precipitated particles in a SCF antisolvent precipitation chamber.

DESCRIPTION OF THE PRIOR ART

A number of industries have experienced a long-felt need for particle micronization and nanonization. The need for an apparatus or method capable of producing sub-micron and nano-sized particles is particularly pronounced in the field of pharmaceutics. Conventional techniques for particle-size reduction currently practiced suffer from many disadvantages. These conventional methods involve either mechanical comminution (crushing, grinding, and milling) or recrystallization of the solute particles from liquid solutions. The limitations of mechanical comminution for particle-size reduction are the shock sensitivity associated with the solid, thermal degradation due to heat generation during mechanical comminution, lack of brittleness of some solids (e.g., most polymers), and chemical degradation due to exposure to the atmosphere.

Conventional recrystallization of solutes from liquid solutions exploits the dependence of a compound's solubility on temperature and/or mixture composition. By changing the temperature, or adding antisolvents to selectively remove the solvent in which the solid is solubilized, the desired material may be precipitated or crystallized from solution to form particles. Crystallization by either solvent evaporation or solvent extraction of a solute usually requires the use of toxic organic antisolvents, surfactants and oils, and yields wet particles that require further drying to remove traces of adsorbed solvent residues. Freeze drying tends to produce particles with broad size distribution that require further drying. Spray drying usually requires evaporation of solvent in a hot fluidized air bed. The high temperatures can degrade sensitive drugs and polymers. Monodisperse particle-size distribution with consistent crystal structure and crystalline properties is also difficult to attain using the above-noted techniques.

Within the last decade, processes for the production of micron and sub-micron sized particles have emerged that use either a supercritical fluid (i.e., a fluid whose temperature and pressure are greater than its critical temperature ($T_c$) and critical pressure ($P_c$)), or compressed fluids in a liquid state. A characteristic of a substance above its critical temperature is that it cannot be condensed regardless of the exerted pressure. It is well known that at near-critical temperatures, large variations in fluid density and transport properties from gas-like to liquid-like can result from relatively moderate pressure changes around the critical pressure (0.9–1.5 $P_c$). While liquids are nearly incompressible and have low diffusivity, gases have higher diffusivity and low solvent power. Supercritical fluids can be made to possess an optimum combination of these properties. The high compressibility of supercritical fluids (implying that large changes in fluid density can be brought about by relatively small changes in pressure, making solvent power highly controllable) coupled with their liquid-like solvent power and better-than-liquid transport properties (higher diffusivity, lower viscosity and lower surface tension compared with liquids), provide a means for controlling mass transfer (mixing) between the solvent containing the solutes (such as a drug or polymer, or both) and the supercritical fluid.

Two processes that use supercritical fluids for particle formation are: (1) Rapid Expansion of Supercritical Solutions (RESS) (Tom, J. W. Debenedetti, P. G., 1991, *The Formation of Bioerodible Polymeric Microspheres and Microparticles by Rapid Expansion of Supercritical Solutions.* BioTechnol. Prog. 7:403–411), and (2) Gas Anti-Solvent (GAS) Recrystallization (Gallagher, P. M., Coffey, M. P., Krukonis, V. J., and Klasutis, N., 1989, *Gas Antisolvent Recrystallization: New Process to Recrystallize Compounds in Soluble and Supercritical Fluids.* Am. Chem. Sypm. Ser., No. 406; U.S. Pat. No. 5,360,478 to Krukonis et al.; U.S. Pat. No. 5,389,263 to Gallagher et al.). See also, PCT Publication WO 95/01221 and U.S. Pat. No. 5,043,280 which describe additional SCF particle-forming techniques.

In the RESS process, a solute (from which the particles are formed) is first solubilized in supercritical $CO_2$ to form a solution. The solution is then sprayed through a nozzle into a lower pressure gaseous medium. Expansion of the solution across this nozzle at supersonic velocities causes rapid depressurization of the solution. This rapid expansion and reduction in $CO_2$ density and solvent power leads to supersaturation of the solution and subsequent recrystallization of virtually contaminant-free particles. The RESS process, however, is not suited for particle formation from polar compounds because such compounds, which include drugs, exhibit little solubility in supercritical $CO_2$. Cosolvents (e.g., methanol) may be added to $CO_2$ to enhance solubility of polar compounds; this, however, affects product purity and the otherwise environmentally benign nature of the RESS process. The RESS process also suffers from operational and scale-up problems associated with nozzle plugging due to particle accumulation in the nozzle and to freezing of $CO_2$ caused by the Joule-Thompson effect accompanying the large pressure drop.

The relatively low solubilities of pharmaceutical compounds in unmodified carbon dioxide are exploited in the second process wherein the solute of interest (typically a drug, polymer or both) is dissolved in a conventional solvent to form a solution. The preferred ternary phase behavior is such that the solute is virtually insoluble in dense carbon dioxide while the solvent is completely miscible with dense carbon dioxide at the recrystallization temperature and pressure. The solute is recrystallized from solution in one of two ways. In the first method, a batch of the solution is expanded several-fold by mixing with dense carbon dioxide in a vessel. Because the carbon dioxide-expanded solvent has a lower solvent strength than the pure solvent, the mixture becomes supersaturated forcing the solute to precipitate or crystallize as microparticles. This process was termed Gas Antisolvent (GAS) recrystallization (Gallagher et al., 1989).

The second method involves spraying the solution through a nozzle into compressed carbon dioxide as fine droplets. In this process, a solute of interest (typically a drug, polymer or both) that is in solution or is dissolved in a conventional solvent to form a solution is sprayed, typically through conventional spray nozzles, such as an orifice or capillary tube(s), into supercritical $CO_2$ which diffuses into the spray droplets causing expansion of the solvent. Because the $CO_2$-expanded solvent has a lower solubilizing capacity than pure solvent, the mixture can become highly supersaturated and the solute is forced to precipitate or crystallize. This process has been termed in general as Precipitation with Compressed Antisolvents (PCA)(Dixon, D. J.; Johnston, K. P.; Bodmeier, R. A. *AIChE J*. 1993, 39, 127–139.) and employs either liquid or supercritical carbon dioxide as the antisolvent. When using a supercritical antisolvent, the spray process has been termed Supercritical Antisolvent (SAS) Process (Yeo, S. -D.; Debenedetti, P. G.; Radosz, M.; Schmidt, H. -W. *Macromolecules* 1993, 26, 6207–6210.) or Aerosol Spray Extraction System (ASES) M üller, B. W.; Fischer, W.; Verfahren zur Herstellung einer mindestens einen Wirkstoff und einen Träger umfassenden Zubereitung, German Patent Appl. No. DE 3744329 Al 1989).

PCT Publication WO 95/01221 teaches the use of a coaxial nozzle for the co-introduction into a vessel of a supercritical fluid and solutions in concurrent directions of flow. Such nozzles achieve solution breakup through the impaction of the solution by a relatively higher velocity fluid. The high velocity fluid creates high frictional surface forces causing solution disintegration into droplets. Any potential high energy waves generated with nozzles described in the prior art are random and originate from impaction and frictional effects of the high velocity fluid on the solution or secondary impaction of multiple vehicle droplets. For purposes of clarity, such high energy waves are defined as Type I waves.

High frequency sound waves can be generated via various types of transducers such as piezoelectric, magnetostrictive, electromagnetic, pneumatic devices (so-called whistles similar to the common whistle based on the organ-pipe effect) and other mechanical transducers. The use of sound waves produced by one or more of these devices to generate droplets from liquid surfaces or to atomize liquid spray jets has been known for more than half-a-century (see Ensminger, "*Ultrasonics: Fundamentals, Technology, Applications*", 2d Ed., Marcel Dekker, 1988 for numerous examples).

One of the earliest 'pneumatic devices' used to generate sound waves employed a jet of air impinging on a cavity to generate sound waves—the so-called Hartmann whistle (J. Hartmann, "*Construction, Performance and Design of the Acoustic Air-Jet Generator*", Journal of Scientific Instruments, 16, 140–149, 1939). In the Hartmann whistle, a jet of air, with velocities reaching Mach 1, is directed into a hollow cavity. The impact at the bottom of the cavity causes a rise in pressure, which in turn causes a counter flow of the energizing gas. The momentum of this counterflow of fluid causes a pressure rarefaction in the cavity. When the force of the jet overcomes the momentum, the flow direction again reverses toward the bottom of the cavity to complete the pressure cycle and propagating a sound wave. Focusing the generated sound waves on spray jets has been employed to atomize liquid spray-jets. It must be appreciated that because the smallest practical focal region of a wave is a sphere one wave-length in diameter, the focal region of a focused sound wave is relatively large as compared to a focused light wave.

Whistle-type devices have been used to generate high-intensity sound waves in both air and liquids. A practical upper frequency for applications using air is approximately 30 kHz. Using helium or hydrogen, such whistles are capable of generating ultrasonic energy in air up to 500 kHz. It is generally recognized in the field that the effectiveness of the device in an application correlates with the frequency (or inversely with the wavelength). The efficiency (ratio of radiated power to the power delivered to the transducer) for such has been reported between <5% to 14%. It is also recognized in the field that the effectiveness of the device does not necessarily correlate with its efficiency. In other words, a low-efficiency nozzle can be highly effective in producing desired droplet sizes.

Whistles for generating sound waves in liquid have also been developed for industrial use. Since the velocity of sound is considerably higher in liquids than in gases, jet velocities equal to the velocity of sound are impractical in liquids. The whistles of W. Janovsky and R. Pohlmann (Zeitschrift für Angewandte Physik, 1, 222, 1948) operate on the jet-edge principle, wherein a high-pressure jet of the liquid or liquids is impinged on the edge of a thin plate which is mounted at the displacement nodes. The plate vibrates in flexure at resonance producing low-frequency waves, typically on the order of magnitude of 5000 Hz. Such "liquid whistles" have been used to produce emulsions or dispersions of one dense medium in another dense medium (oil/water, mercury/water, etc.) In many instances, especially in the pharmaceutical industry, it is desired to coat core particles or medicaments. Generally, such coating has been carried out using techniques such as electrolysis, vapor deposition, and fluidized bed or air suspension techniques. However, these methods all suffer from various drawbacks, e.g., the difficulty in maintaining aseptic conditions, the inability to generate extremely fine particles for coating purposes and solvent emission control.

SUMMARY OF THE INVENTION

The present invention provides improved near- or super-critical fluid processes for the precipitation of extremely small particles having average diameters (inferred from SEM photographs) on the order of from about 0.1–10 $\mu$m and most preferably up to about 0.6 $\mu$m. The methods of the invention find particular utility as methods for particle micronization and nanonization, particularly in the field of pharmaceutics. However, the methods of the invention can also be used in other fields such as those related to foods, chemicals, polymers, pesticides, explosives, coatings and catalysts wherein benefits are obtained from a decrease in particle sizes and concomitant increases in particle surface areas.

Broadly speaking, the methods of the invention involve precipitation of extremely small particles which can be recovered as particles, or deposited on core particles to form composite products. In all cases however, the methods of the invention involve contacting a fluid dispersion (e.g., a gas or liquid solution or suspension) including a continuous phase dispersant with at least one substance (e.g., a medicament such as a drug) dispersed in the dispersant with an antisolvent at near- or supercritical conditions for the antisolvent, so as to cause the antisolvent to deplete the dispersant and precipitate the substance as extremely small particles. Conditions are established during the contacting step so as to enhance the mass transfer rate between the antisolvent and the dispersant so that particle nucleation and precipitation occur rapidly.

In most cases, the fluid dispersions of the invention would be in the form of liquid solutions, i.e., the dispersant is a solvent and the substance to be precipitated is a solute dissolved in the solvent. Moreover, the dispersants should comprise at least about 50% by weight (and more preferably at least about 90% by weight) of the overall dispersions. The conditions established during the dispersion/antisolvent contacting step are typically in the range of from about 0.7–1.4 $T_c$ and from about 0.2–7 $P_c$ of the antisolvent; more preferably, these ranges are from about 1–1.2 $T_c$ and from about 0.9–2 $P_c$ of the antisolvent. Preferably, the conditions during contact are maintained so that the dispersant and antisolvent are essentially completely miscible in all proportions thereof.

The antisolvents used in the invention are normally selected from the group consisting of carbon dioxide, propane, butane, isobutane, nitrous oxide, sulfur hexafluoride and trifluoromethane, with carbon dioxide being the single most preferred antisolvent for reasons of cost and ease of processing. In all cases, the antisolvent should be substantially miscible with the dispersant while the substance or medicament to be precipitated should be substantially insoluble in the antisolvent, i.e., the substance or medicament, at the selected dispersion/antisolvent contacting conditions, should be no more than about 5% by weight soluble in the antisolvent, and preferably is essentially completely insoluble.

In one preferred aspect of the invention, improved spray processes are provided for precipitation of extremely small particles. For example, use may be made of specialized nozzles for creating extremely fine droplet sprays of the fluid dispersions into a precipitation zone containing antisolvent. Using such equipment, the methods of the invention involve passing the fluid dispersion through a first passageway and first passageway outlet into the precipitation zone containing the antisolvent and maintained at the above-defined near- or supercritical conditions of temperature and pressure for the antisolvent. Simultaneously, an energizing gas stream is passed along the second passageway and through a second passageway outlet proximal to the first fluid dispersion outlet. The passage of such an energizing gas stream through the second outlet generates high frequency waves of the energizing gas adjacent the first passageway outlet in order to break up the fluid dispersion into extremely small droplets. This causes the antisolvent in the precipitation zone to deplete the dispersant and rapidly precipitate small particles of the substance.

The preferred process of the invention involves deliberate generation of high energy sonic waves (Type II waves) in addition to and substantially independent of any impaction and frictional forces typical of prior art nozzles (Type I waves). Type II sonic waves may be generated in the energizing gas stream or in the dispersion itself. In the former situation, specialized nozzles as described below are used, and in the latter, a starting dispersion may be sprayed onto a sonicating surface coupled to a transducer (e.g., piezoelectric, magnetostrictive, or electromagnetic), and the resultant particles are contacted with turbulent SCF fluid.

In preferred forms, the specialized nozzle is of the type commercialized by Sonimist of Farmingdale, N.Y. as Model 600-1. This nozzle includes an elongated body presenting a central tube which serves as the primary spray nozzle for the dispersions of the invention. The nozzle structure also includes a secondary passageway in surrounding relationship to the central tube for passage of the energizing gas along the length of the central tube and out the nozzle outlet. The secondary passageway for the energizing gas is configured to present a converging section defining a restricted throat, with a diverging section downstream from the throat and leading to the nozzle outlet. In addition, the diverging portion of the secondary passageway is equipped with a radially expanded, annular resonator cavity for reflecting sound waves. The outlet end of the central tube is located downstream of the constricted throat.

Use of nozzles of this type serves to generate and focus the preferred high frequency sonic waves of energizing gas which has been shown to maximize the production of extremely small dispersion droplets in the precipitation zone, thereby leading to the precipitation of the very small particles of the invention. The frequency of the generated waves of energizing gas could range anywhere from 0.5 kHz to 300 kHz, and more preferably from about 10–100 kHz. It is believed that the inherent kinetic energy of the energizing gas stream is converted to acoustic energy by virtue of passage of the energizing gas stream through the restricted throat, resonator cavity and outlet of the nozzle. Generally, at least about 1% (more preferably from about 2–14%) of the kinetic energy of the energizing gas stream is converted to acoustic energy.

In preferred forms, the energizing gas is the same as the selected antisolvent, and in most cases carbon dioxide is used both as the antisolvent and energizing gas. More broadly however, the energizing gas may be selected from the group consisting of air, oxygen, nitrogen, helium, carbon dioxide, propane, butane, isobutane, trifluoromethane, nitrous oxide, sulfur hexafluoride and mixtures thereof.

Where it is desired to coat core particles with a desired substance, a fluid dispersion of the type described is sprayed into an enclosed precipitation zone containing a quantity of antisolvent at near-or supercritical conditions for the antisolvent. Simultaneously, a turbulent fluidized flow of the core particles is created within the precipitation zone by passing a fluidizing gas stream comprising the selected antisolvent into the precipitation zone. Conditions are maintained in the zone so that the antisolvent rapidly depletes the dispersant and precipitates the substance as small particles onto the fluidized core particles. Although the specialized nozzle arrangement described above can be used in the coating methods of the invention, such is not generally required. That is, in coating applications, the coating particles can typically be relatively larger without detracting from the usefulness of the final product; accordingly, conventional capillary nozzles and the like can be used to good effect in such coating processes.

In one form, the fluidized flow of core particles is established by passing the fluidizing gas stream in a direction which is substantially countercurrent to the direction of fluid dispersion spray into the precipitation zone. However, where modified Wurster coating devices are employed, the fluidizing gas stream is directed co-current relative to the direction of fluid dispersion spray. It is important that at least a part of the fluidizing gas stream be made up of the antisolvent, particularly where countercurrent fluidizing stream flow is employed. In any case, however, the fluidizing gas stream should normally have a concentration of antisolvent therein of at least about 70% by weight and more preferably the fluidizing gas stream consists essentially of antisolvent.

A wide variety of core particles can be used in the invention but generally these should have a maximum dimension of up to about 15 mm, and more preferably up to about 1 mm. Core particles such as glass or sugar beads can be used and in pharmaceutical applications, it is contemplated that medicament tablets or other discrete solid dosage forms can be coated. The final coated products can range from micron-sized to several millimeters. In the case of medicaments, depending upon the application, the final coatings would typically have a thickness of from about 0.1 $\mu$m to 2 mm (more preferably from about 1–500 $\mu$m), and the coating would be from about 1–30% (more preferably from about 5–15%) by weight of the final coated product.

In another aspect of the invention, a process is provided for the preparation and administration to a patient of a particulate medicament without the necessity of transferring the medicament between containers, i.e., the dispersion/antisolvent precipitation is carried out in a final use container which is subsequently sealed and permits withdrawal of medicament dose(s) from the use container. Generally, this method involves lyophobic precipitation of medicaments which may be performed in a batch or semi-batch mode.

In preferred forms, the following general steps are performed: (a) the medicament is dissolved in an organic solvent to form a solution or suspension; (b) the solution or suspension is sterile filtered; (c) the solution or suspension is either metered into the final use container prior to contact with the supercritical fluid (batch mode) or continuously as a spray with supercritical fluid contact (semi-batch mode); (d) the medicament suspension or solution in the container is contacted with the supercritical fluid until, at a predetermined concentration of supercritical fluid the mixed, expanded liquid is no longer a solvent for the medicament and particle precipitation is effected; (e) the use container is purged with supercritical fluid until the organic solvent is completely depleted from the system; and (f) the finished solid particulate medicament is aseptically sealed in the use container. Thereafter, when it is desired to use the medicament, a liquid carrier may be placed in the use container to form a mixture, which can then be administered by injection or the like.

DETAILED DESCRIPTION OF THE PREFERRED EMBODIMENTS

The following Examples set forth techniques, compositions, and system parameters, as well as test results, demonstrating various aspects of the present invention. Examples 1–4 relate primarily to the particle micronization and nanonization aspects of the invention, whereas Examples 5–8 pertain to particle coating; the remaining examples illustrate production of finished products by lyophobic precipitation. It is to be understood, however, that these examples are presented by way of illustration only and that nothing therein should be taken as a limitation upon the overall scope of the invention.

PARTICLE MICRONIZATION AND NANONIZATION

Equipment and Experimental Procedures for Examples 1–4

Figure 1:
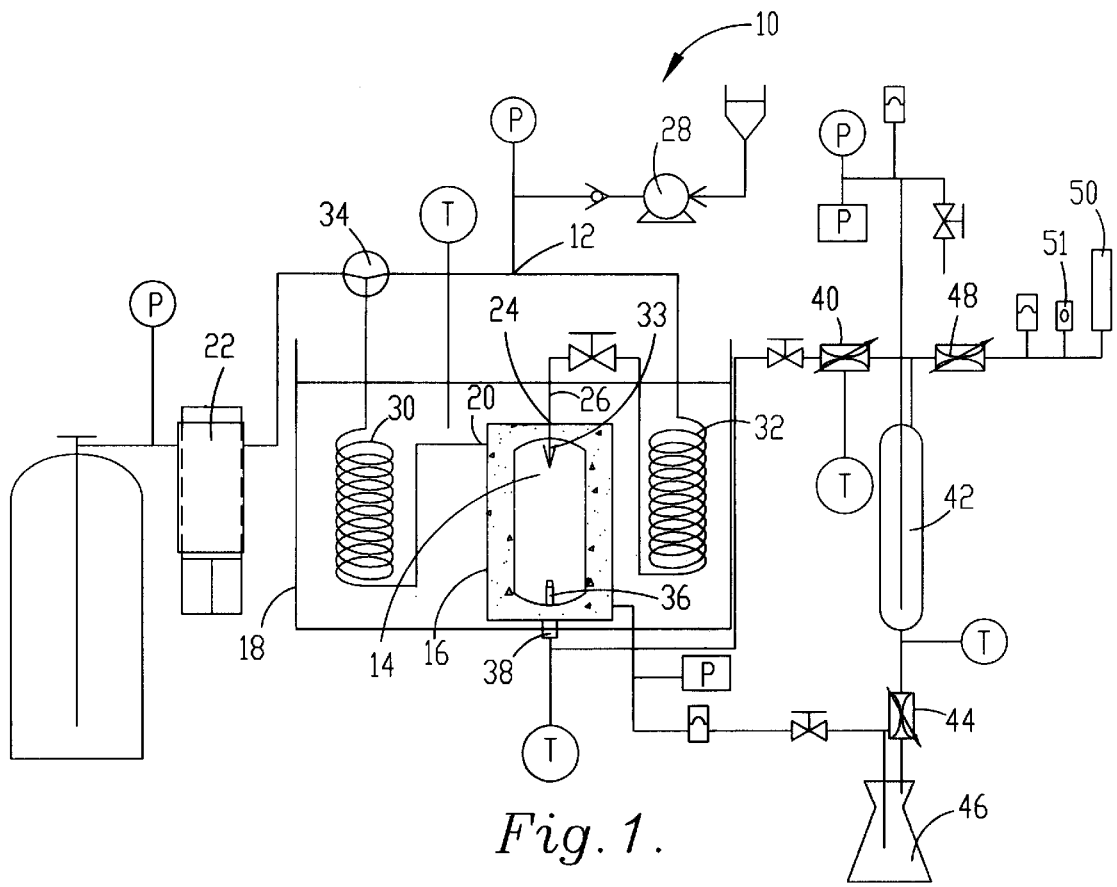
FIG. 1 is a schematic of the apparatus for the conventional SAS recrystallization from organic solutions.

FIG. 1 shows a schematic of the apparatus 10 used for particle recrystallization from organic solvents using the conventional SAS process. The experimental unit 10 allowed SAS experiments to be conducted in either batch or semi-continuous mode at pressures up to 5,000 psi and temperatures up to 70° C. The mixing of solvent and antisolvent occurred at two different locations 12, 14 within the unit. Unit 10 provided versatility in setting the operating parameters.

The unit 10 was built around a 65 ml high pressure Jerguson gauge (Burlington, Mass.) view cell 16. The cell 16 was equipped with a sapphire window that allowed viewing of the expansion and crystallization process. The cell 16 was housed in a heated, isothermal, transparent acrylic water bath 18. This water bath 18 was used for maintaining the cell 16 at a desired temperature (20°–70° C.). When the bath temperature was stable at a desired value, $CO_2$ was pumped through the top side port 20 of the cell 16 with an ISCO (Lincoln, Nebr.) 260D syringe pump 22 at a constant rate (typically 5 ml/min. of liquid $CO_2$) until the pressure in the cell 16 reached a desired level (1,500 psi). When temperature and pressure in the cell 16 were stabilized, the organic solution (DMSO or ethyl acetate solution of drug and/or polymer) was metered from the top central port 24 of the cell 16 through a stainless steel, 1/16" O.D., 100 μm I.D. capillary nozzle tubing 26 using a Milton Roy (Riviera Beach, Fla.) 396-89 minipump 28. It was found that a minimum solution flow rate of 2.5 ml/min. was needed to consistently obtain a jet spray. Both fluids were preheated to operating temperature by passing through heat exchangers 30, 32 housed together with the cell 16 in the water bath 18.

Fresh $CO_2$ and the organic solution streams mixed at location 14, which is just downstream of the nozzle tip 33 at the top of the cell 16. A cloudy zone about 1 cm long was seen to form in this area indicating intimate mixing of the fluids and particle formation. Solvent depletion from the spray droplets causes the drug and/or polymer dissolved in the organic solvent to nucleate. The resulting particles descended down the cell. Alternatively, the streams can be premixed prior to reaching the nozzle tip 33 using the two-way valve 34.

Particles descending down the cell 16 either adhered to the cell walls or were collected on a 6" long glass rod 36. Particles larger than 0.5 μm leaving the view cell chamber were retained on a 0.5 μm stainless steel frit housed in the T-shaped fitting at the central bottom port 38. A thermocouple inserted through this fitting was used to monitor the cell temperature. The drug and/or polymer depleted mixture of $CO_2$ and organic solution flowed through a step-motor controlled, heated micrometering valve assembly 40. Upon expansion to a subcritical pressure (typically close to atmospheric pressure), the mixture separated into an organic liquid phase and a $CO_2$ gas phase. Phase separation took place in the flash drum 42; the organic solution flowed through a micrometering valve 44 and was collected in a vessel 46. The solution was then analyzed for drug and polymer content. $CO_2$ was vented through a second micrometering valve 48, a rotameter 51, and an electronic mass flowmeter 50.

Typically, the solution was pumped for 15 minutes in order to produce a statistically representative sample of drug and/or polymer microparticles. Following this, the flow of organic solution was stopped while the $CO_2$ flow was continued for another 1.5 hours in order to flush out any organic phase left in the cell, and to dry the collected particles. It was found that flowing $CO_2$ at 1,500 psig for 1.5 hours was adequate for flushing out the organic solvent present in the cell and for drying the particles. Following the drying period, the pressure was decreased to atmospheric level at a rate of −50 psi/min. Particle samples were collected from the cell window, the porous frit, and the glass tube, and were analyzed by scanning electron microscopy (SEM) to estimate particle size and morphology.

Accurate pressure control was essential in the highly compressible near-critical region. Pressure fluctuations in this region have a strong effect on the level of expansion of the organic solution and thus on the level of supersaturation and, consequently, on crystal growth and crystal size distribution. Pressure control in the cell 16, along with monitoring of pressure, temperature, and flow rate, were accomplished using the Camile® (Midland, Mich.) 2500 Data Acquisition and Control system. A 100 steps/revolution stepping motor, operating at 200 half-steps/revolution, was used to actuate the heated micrometering valve 54. Pressure control was achieved using an HC-11 microprocessor that interprets the output from the Camile PID controller and acts as a stepmotor controller. The software program allowed the microprocessor to seek a window wherein the valve will operate to provide pressure control within transducer precision (±10 psi).

Figure 2:
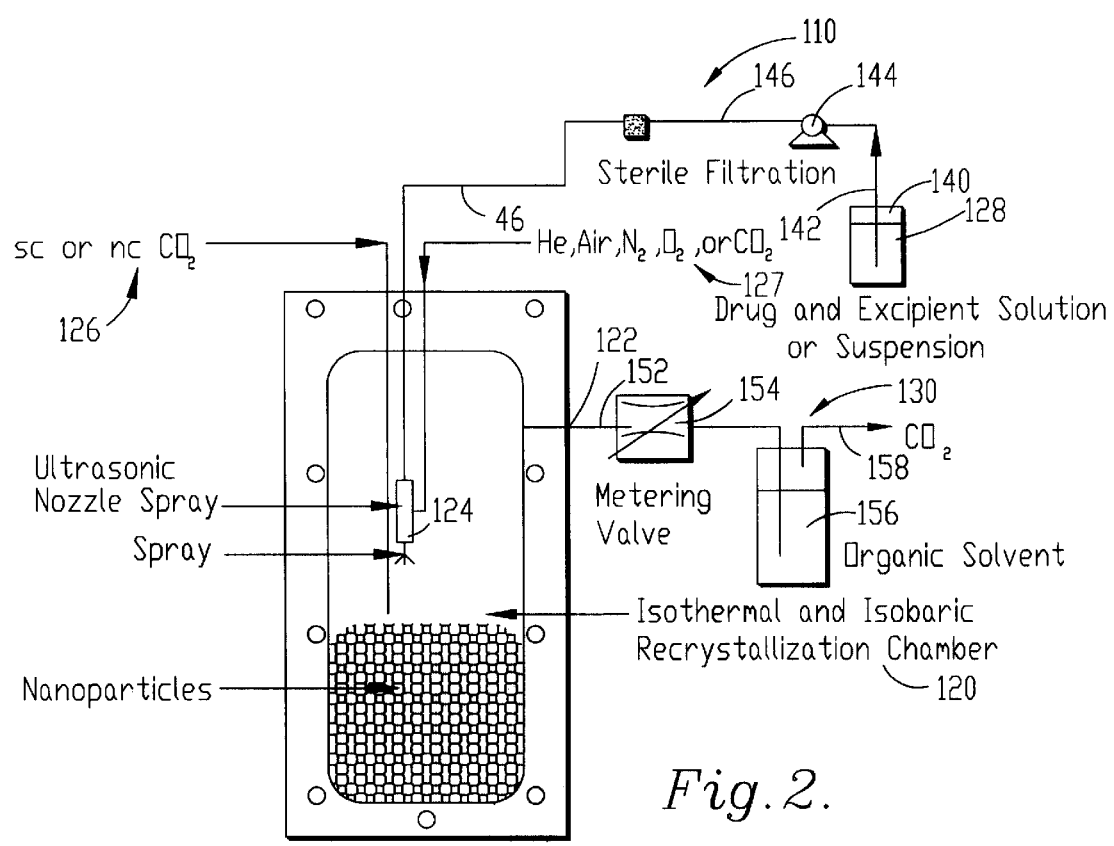
FIG. 2 is a schematic representation of an apparatus useful in the practice of the invention.

FIG. 2 shows schematically an apparatus 110 according to the present invention. Apparatus 110 is identical to apparatus 10 with the exception that the view cell serving as crystallization chamber is replaced with a larger (450 ml), stainless steel vessel that can house the nozzle. Here again, the crystallization chamber was housed in an isothermal water bath, and pressure is controlled as described previously with regard to the conventional SAS process (FIG. 1). In apparatus 110, an organic solvent such as dimethyl sulfoxide (DMSO), in which solutes such as drug, polymer, and/or excipient materials are solubilized, is also sprayed as a fine mist into a chamber containing a near-critical or supercritical antisolvent.

In more detail, apparatus 110 of the present invention includes an isothermal and isobaric recrystallization chamber 120, a spray nozzle 124, a source of supercritical (sc) or near-critical (nc) $CO_2$ 126, a source of compressed gas 127 which serves to energize the nozzle 124, a drug and excipient solution 128, an organic solvent collection vessel 156, and a $CO_2$ outlet header 130.

The drug and excipient solution is drawn from vessel 140 through line 142 by pump 144 and is discharged through line 146 into chamber 120 through line 146 as shown in FIG. 2.

The nozzle 124 is attached to the end of line 146 within chamber 120. Energizing gas for the nozzle consisting of He, $N_2$, $O_2$, air, $CO_2$, other supercritical fluids, or a mixture thereof, from source 127 is admitted through line 150 into chamber 120, as shown in FIG. 2. The near-critical or supercritical fluid (antisolvent) is admitted from source 126. Alternatively, if the energizing gas is supercritical (or near-critical), source 127 also can be used for admitting the supercritical fluid into chamber 120; source 126 then may be either not employed, or used for admitting a supercritical fluid in the same composition as in source 124, or a supercritical fluid of different composition. This latter alternative can be used for either increasing or decreasing the concentration gradients between the antisolvent phase and the buffer zone. The solute-depleted organic solvent and solvent-loaded $CO_2$ are removed from chamber 120 via outlet 122 through line 152 and metering valve 154 into flash drum 156, in which $CO_2$ is allowed to separate from the liquid organic solvent. The $CO_2$ is allowed to vent from vessel 156 through vent line 158.

Figure 3:
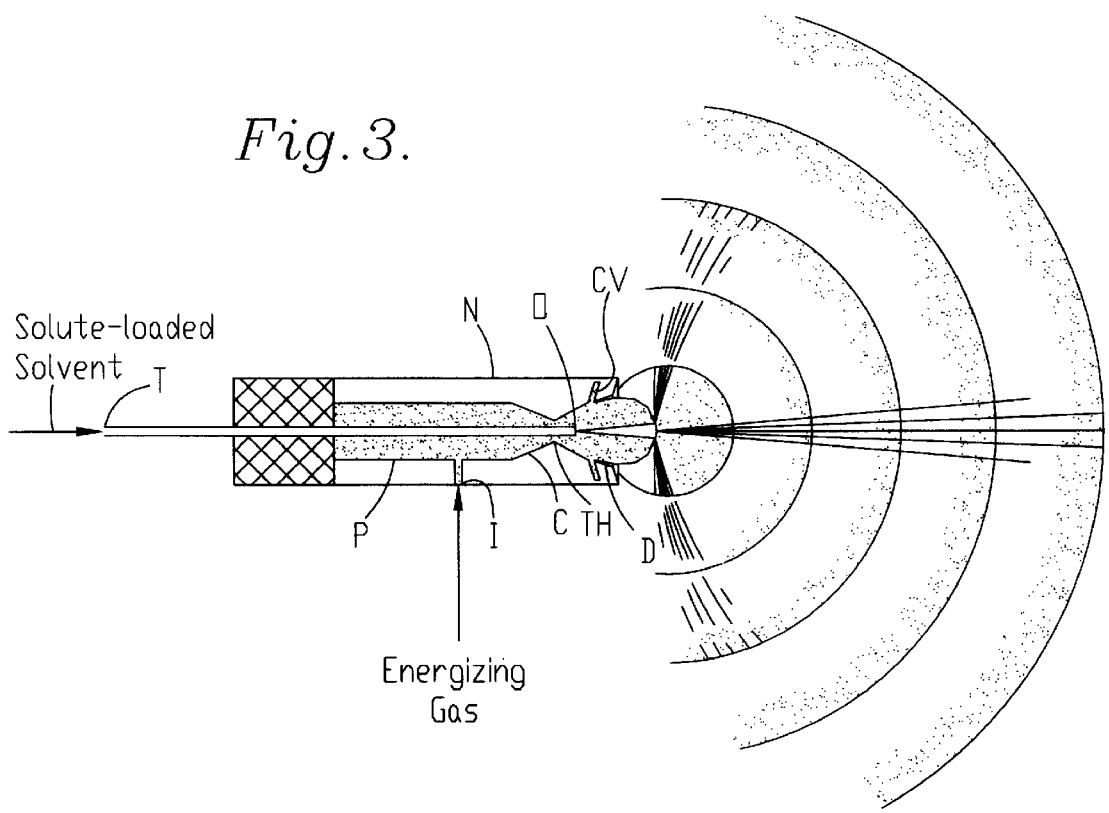
FIG. 3 is a schematic cross-sectional view of the nozzle employed in the practice of the invention.

FIG. 3 is a schematic of a nozzle (Sonimist, Farmingdale, N.Y., Model 600-1) employed in apparatus 110. This nozzle N is of the convergent-divergent type and includes a central capillary-type tube T presenting an outlet O. The nozzle N further includes a surrounding passageway P presenting an inlet I for energizing gas. The passageway P includes a converging section C presenting a restricted throat TH and a downstream diverging section D. The section D includes a radially expanded, annular resonator cavity CV. It is to be noted that the outlet O of the tube T is positioned downstream of the throat TH. The nozzle N is energized by compressed gas (conventionally a light gas such as air, He, $O_2$, or $N_2$ and in the present invention preferably through use of antisolvent gas). A sonic field (Type II waves) is created at the throat TH of the nozzle N as the energizing gas accelerates and reaches the velocity of sound or greater. These high frequency waves impinge upon the entrance of a resonator cavity CV, and the latter serves to produce high frequency waves of the energizing gas, producing a chopping effect that breaks up the liquid jet comprising the solute-loaded solvent into extremely small droplets.

In the FIG. 3 device, the generated sonic waves are focused on the dispersion spray in order to facilitate enhanced atomization of the spray. For precipitation to occur, the dispersant from the droplets must be transferred to the antisolvent phase surrounding the droplets. In addition to enhancing atomization, the concomitant increase in the mass transfer surface area produced by the sonic waves enhances the mass transfer rate between the droplets formed and the surrounding fluid medium, thereby increasing the rate of solid precipitation.

When spraying into ambient air, with 20–100 psig back pressure of energizing gas, the Sonimist nozzle produces a fine, evenly dispersed spray of droplets having diameters in the range of 0.1–50 $\mu$m depending on operating conditions. Mean droplet diameters of 1–10 $\mu$m are obtained when spraying water into ambient atmosphere. If interphase mass transfer does not significantly interfere with the atomization process, droplet sizes are expected to be even smaller when spraying into a higher pressure gaseous environment or when using organic solvents with lower surface tension and viscosity than water.

When using this nozzle, the flow rate of the energizing gas should be such that sonic velocities are attained by the energizing gas at the throat of the nozzle. While in conventional use of this nozzle, a pressure differential of 2 atm between the energizing gas and ambient atmosphere is sufficient to achieve this sonic velocity, this pressure differential is not sufficient when operating at near-critical or supercritical conditions. The following equation is used to estimate whether a discharge velocity is subsonic (Perry and Chilton, 1973, Chemical Engineer's Handbook, 5th Ed., McGraw Hill, Chap. 5):

$$P_2/P_0 > [2/(k+1)]^{k/k-1}$$

where $P_0$ is the energizing gas pressure, $P_2$ is the nozzle outlet pressure, and k is the ratio of heat capacities at constant pressure and constant volume of the gas (i.e., $C_p/C_v$). For instance, for a pressure of 1,500 psig at the nozzle exit and an energizing gas ($CO_2$) pressure of 6,000 psig, $P_2/P_0 = 1,500/6,000 = 0.25$; $C_p/C_v$ at 1,500 psig=4.81; and $[2/(k+1)]^{k/k-1} = 0.26$. Hence $P_2/P_0 < [2/(k+1)]^{k/k-1}$ and the velocity can be sonic.

While the above example illustrates conditions under which sonic velocities may be estimated, such high velocities may not be required for all applications. For instance, it has been found that using a chamber pressure of 1,250 psig and an energizing gas pressure of 1,850 psig provides enough energy to reduce particle size substantially. A one order of magnitude reduction in particle size (when compared to results obtained by conventional SAS recrystallization) was also observed when using only 100 psig pressure differential between the chamber held at 1,500 psig and the energizing gas ($CO_2$). Thus, the nozzle illustrated in FIG. 3 can be used in a wide range of operating conditions in order to substantially reduce particle size and to increase surface area. Broadly speaking, the energizing gas should be delivered to the nozzle N at a pressure of from about 1100–6000 psig, more preferably from about 1500–2500 psig, and at a temperature such that upon expansion, the energizing gas attains the desired temperature of the recrystallization chamber. The frequency of the waves of antisolvent created at the nozzle outlet should be at least about 0.5 kHz and more preferably from about 10–100 kHz.

Furthermore, the invention may be practiced without the use of the nozzle illustrated in FIG. 3. The invention may be practiced with any nozzle that provides a means for using a gaseous (or near-critical or supercritical fluid) stream as energizing medium to atomize the sprayed solution into smaller droplets and/or to create turbulence around the spray droplets which increases the mass transfer rates between the droplet and antisolvent phases. Both converging-diverging nozzles as well as converging nozzles may be employed in the present invention.

EXAMPLES 1–4

Comparison of Particles Produced by the Conventional SAS Process and the Process of the Present Invention In these examples, the recrystallization of hydrocortisone, poly (D,L-lactide-glycolide) copolymer (RG503H), ibuprofen, and camptothecin was studied. The recrystallization of hydrocortisone and RG503H was performed using both the conventional SAS process as well as the present invention.

Hydrocortisone is a common anti-inflammatory agent and ibuprofen is a common pain reliever. They were acquired from Sigma Chemical Co., St. Louis, Mo., and were used without further purification. Camptothecin is an anti-cancer drug with a very low aqueous solubility; reduction in its particle size or an increase in its particle surface area can substantially increase its dissolution rate and render it therapeutically more useful. RG503H was acquired from Henley, Montvale, N.J. It contains a 1:1 molar ratio of lactide and glycolide and has an inherent viscosity in chloroform of 0.3. RG503H is FDA approved for administration to humans, is non-toxic, non-tissue reactive, biodegrades to non-toxic products, and is particularly suited for surgical sutures. PLGA copolymers have been the subject of intense micronization and microencapsulation studies.

Certified grade DMSO and ethyl acetate (99.9% purity, Fisher Scientific, Fairlawn, N.J.), bone dry $CO_2$ (99.8% purity, Genex, Kansas City) were used without further purification. Particles were collected on a double-sided carbon tape applied to an aluminum SEM tab that was placed in the crystallization chamber prior to each experiment. Particles that were deposited on the cells walls were also collected for analysis. Particle morphology was determined by SEM (Hitachi, Model S-570). Particle size was also estimated by SEM. The SEM samples were sputter-coated with Au/Pd alloy.

Hydrocortisone particles were redissolved in ethyl acetate, and analyzed by GC-FID for trace DMSO contamination. Effluent solutions recovered in the flash drum were also analyzed for hydrocortisone content.

The results of repeat conventional SAS recrystallization experiments are compared in Table 1. Particle size for whisker particles refers to their thickness or width. The data in Table 1 demonstrate that the average particle size for all solutes studied, including HYAFF-7 (the ethyl ester of hyaluronic acid) is reproducible, indicating that the SAS spray technique is a controllable and reproducible recrystallization technique.

TABLE 1

Reproducibility of Morphology and Size of Particles
Formed by the Conventional SAS Recrystallization
Method, as Estimated from SEM Micrographs.
P = 1,500 psig; $CO_2$ Flow Rate = 5 ml/min.;
Solution Flow Rate = 2.5 ml/min;
Capillary Nozzle I.D. = 100 $\mu$m.

| Run | Solvent | Solute | Concentration (mg/ml) | Temp. (°C.) | Particle Morphology | Average Particle Size ($\mu$m) |
|---|---|---|---|---|---|---|
| 4-12 | DMSO | Hydrocortisone | 30 | 35 | Whisker | 1 |
| 4-14 | DMSO | Hydrocortisone | 30 | 35 | Whisker | 1 |
| 4-16 | DMSO | Hydrocortisone | 30 | 35 | Whisker | 1 |
| 12-1 | Ethyl Acetate | RG503H | 10 | 35 | Microsphere | 5–50 |
| 5-8 | Ethyl Acetate | RG503H | 10 | 35 | Microsphere | 10–20 |
| 12-16 | DMSO | RG503H | 2 | 35 | Tubes/Flakes | 25–100 |
| 12-20 | DMSO | RG503H | 2 | 35 | Tubes/Flakes | 25–100 |
| 6-6 | DMSO | HYAFF-7 | 0.5 | 40 | Resin | >100 |
| 6-8 | DMSO | HYAFF-7 | 0.5 | 40 | Resin | >100 |

EXAMPLE 1

Figure 4:
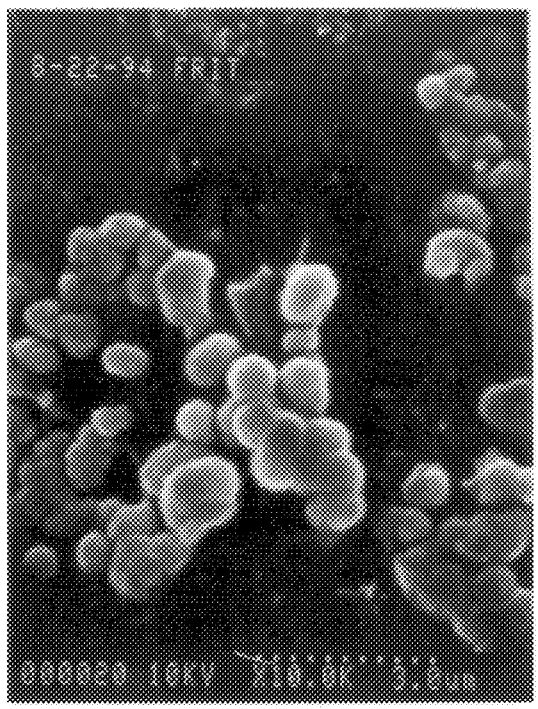
FIG. 4 is an SEM micrograph (10,000× magnification) of hydrocortisone micronized by recrystallization from a 5 mg/ml DMSO solution using the conventional SAS process with a 100 $\mu$m capillary nozzle.
Figure 5:
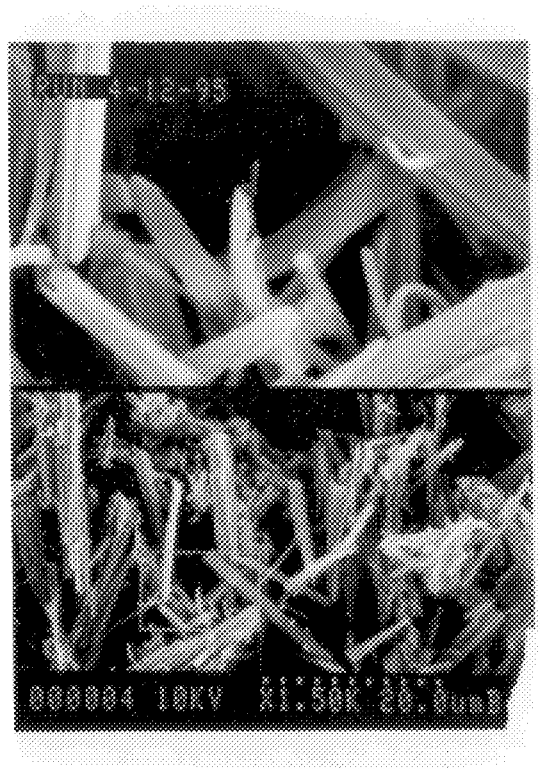
FIG. 5 is an SEM micrograph of hydrocortisone micronized by recrystallization from a 30 mg/ml DMSO solution using the conventional SAS process with a 100 $\mu$m capillary nozzle.

Comparison of Results of Recrystallization of Hydrocortisone from DMSO Solutions Hydrocortisone Particles Produced Using the Conventional SAS Process FIG. 4 shows the SEM micrograph of hydrocortisone particles recrystallized from a 5 mg/ml DMSO solution using the 100 $\mu$m capillary nozzle (P=1,500 psi; T=35° C.; $CO_2$ flow rate=5 m/min.; solution flow rate=2.5 ml/min.). Particles are agglomerated, nearly spherical, and range in size from 0.5–1 $\mu$m. Recrystallization of hydrocortisone from a 30 mg/ml DMSO solution yielded long (up to 1 mm), 1 $\mu$m thick, whisker-shaped particles shown in FIG. 5 (P=1,500 psi; T=35° C.; $CO_2$ flow rate =5 ml/min.; solution flow rate=2.5 ml/min.; capillary I.D.=100 $\mu$m). Note that the magnification level in the upper part of micrograph (b) is five-fold greater when compared to the lower micrograph. Greater nucleation rates should result at this higher concentration, which should lead to the formation of smaller particles (Gallagher et al., 1989); however, it appears that the increase in viscosity at higher solute concentrations and the premature onset of nucleation, and crystallization prior to secondary atomization hinder the atomization process, resulting in the formation of elongated, whisker-like particles. Indeed, the increase in particle size with an increase in solute concentration was observed for all solutes recrystallized using the conventional SAS process.

Figure 6:
FIG. 6 is a GC-FID analysis of hydrocortisone recrystallized from a 30 mg/ml DMSO solution using the conventional SAS process with a 100 $\mu$m capillary nozzle.

Particles size is fairly reproducible. For three runs under these same conditions (30 mg/ml), particle thickness is narrowly distributed and is in the order of 1 $\mu$m. The amount of DMSO in the hydrocortisone particles was below the detection limit of the GC-FID ($\approx$10 ppm) (FIG. 6). It thus appears that the particles are virtually solvent-free.

Hydrocortisone Particles Produced Using the Present Invention in which Compressed $CO_2$ Was Used as Energizing Gas and as Antisolvent For a nozzle exit pressure of 1,500 psig and a temperature of 35° C., calculations indicate that an energizing pressure of roughly 6,000 psig at 55° C. is needed to obtain sonic velocities at the nozzle exit. $CO_2$ must be pumped at a rate such that a 4,500 psig back pressure is established. An experiment using 100 psig back pressure (i.e. 1,600 psig $CO_2$ supply pressure and 1,500 psig at the nozzle exit, corresponding to a $CO_2$ flow rate of 25 ml/min.) yielded hydrocortisone particles consisting of nearly spherical, 0.5–1 $\mu$m in size, and whisker-shaped particles, roughly 1 $\mu$m wide and 10 $\mu$m long. These results suggest that production of smaller particles can be achieved by using $CO_2$ at even sub-sonic velocities to energize the nozzle. Hence, while near-sonic, sonic, and supersonic compressed gas velocities are preferred for production of nanoparticles, even lower compressed gas flow rates can significantly reduce particle size when compared to the conventional SAS process where the antisolvent phase is nearly-stagnant.

Figure 7A:
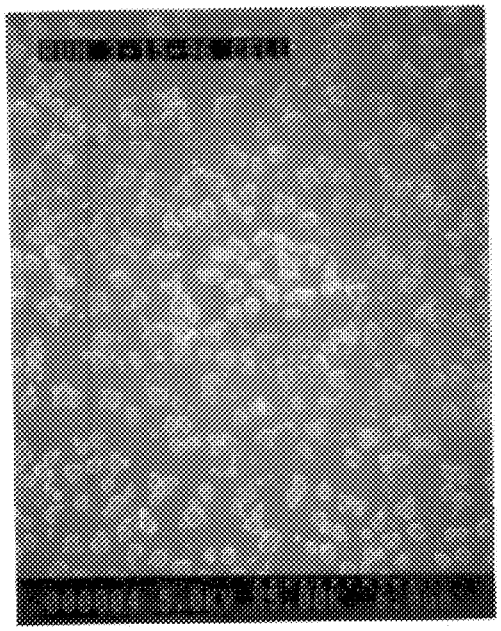
FIGS. 7a and 7b are a pair of SEM micrographs (5,000× and 9,900× magnification, respectively) of hydrocortisone nanonized by recrystallization from a 30 mg/ml DMSO solution using the nozzle of the present invention (compressed $CO_2$ is used as energizing gas and as antisolvent).
Figure 7B:
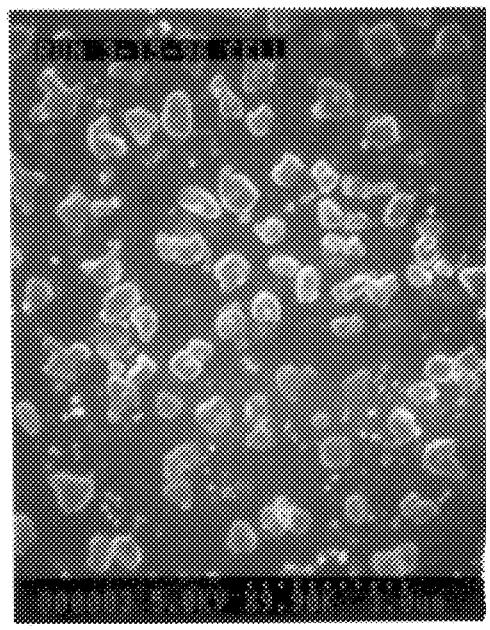

FIGS. 7a and 7b show a pair of SEM micrographs of hydrocortisone particles recrystallized from a 30 mg/ml DMSO solution using the nozzle in FIG. 3, and $CO_2$ as energizing gas. In the recrystallization chamber, P=1,250 psig; T=35° C.; and the solution flow rate=2.5 ml/min. During the period when the solution was pumped (roughly 1 minute), the pressure of $CO_2$ at line 50 (FIG. 2) was equal to 1,850 psig, thereby providing 600 psi of back pressure. $CO_2$ temperature in source 24 (FIG. 2) was brought up to 50° C., so that upon expansion from 1,850 psig to 1,250 psig, the temperature decreased to nearly 35° C., the temperature in the crystallization chamber. This back pressure translated to a $CO_2$ flow rate of 90 ml/min. during the atomization phase. It is observed that the particles are discrete, nearly spherical, and appear to be narrowly distributed around 500 nanometers (nm). Nearly all particles are smaller than 600 nm. These results are in contrast to the 1 $\mu$m wide and nearly 1 mm long fibers observed previously (FIG. 5) when using the 100 $\mu$m capillary nozzle. Hence, a significant decrease in the average particle size is observed with the use of the present invention.

Figure 8:
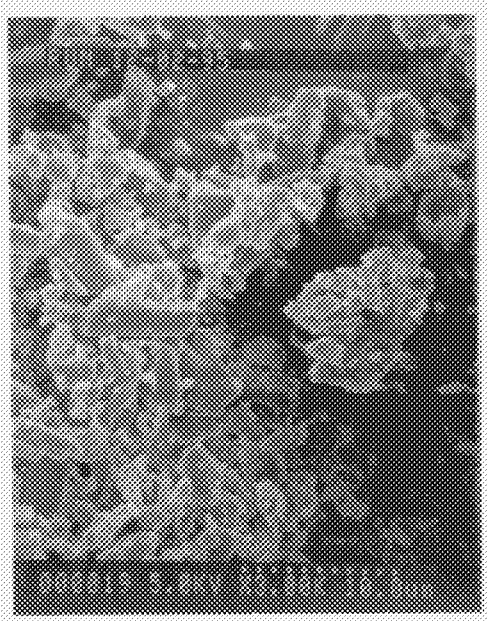
FIG. 8 is an SEM micrograph (3,000× magnification) of hydrocortisone micronized by recrystallization from a 30 mg/ml DMSO solution using the nozzle of the present invention (He is used as energizing gas and compressed $CO_2$ is used as antisolvent).

Hydrocortisone Particles Produced Using the Present Invention in which He Was Used as Energizing Gas and Compressed $CO_2$ Was Used as Antisolvent The 30 mg/ml DMSO solution of hydrocortisone was also recrystallized using He at 1,600 psig as energizing gas and $CO_2$ at 1,500 psig, 35° C. as antisolvent. FIG. 8 demonstrates that it is possible to use a light gas to energize the nozzle. Although these conditions are not optimum, the process still produces particles that are relatively small. Some particles appear to be even smaller than 1 $\mu$m. The merits of using He as opposed to $CO_2$ as energizing gas are not evident from FIG. 8; however, it is anticipated that as the solute concentration and viscosity of the solution is increased, it may be necessary to introduce a gaseous buffer such as He to avoid premature nucleation. When using a light gas to energize the nozzle, the flow rate of the supercritical fluid relative to that of the light gas should be high enough to provide sufficient antisolvent power for the supercritical fluid/light gas mixture. Use of $CO_2$ as both antisolvent and energizing gas, when possible, is advantageous over the use of a light gas as energizing gas because (a) chances for contamination are reduced, (b) the antisolvent power of $CO_2$ is not diminished, (c) required $CO_2$ flow rates are lower, and (d) solvent recovery is efficient.

EXAMPLE 2

Comparison of Results of Recrystallization of RG503H Particles Produced Using the Conventional SAS Process RG503H was recrystallized from solutions of DMSO and ethyl acetate at a pressure of 1,500 psig and a temperature of 35° C. using a 100 $\mu$m capillary nozzle. Neat RG503H particles, as supplied by the vendor, are relatively large, agglomerated precipitates (>50 $\mu$m). Table 2 depicts the effect of RG503H concentration on size and morphology of RG503H recrystallized from solution. RG503H in DMSO appears to recrystallize as tubules at low concentrations, as a mixture of flakes and tubules at medium concentrations, and as precipitates of large amorphous material at higher concentrations.

Figure 9A:
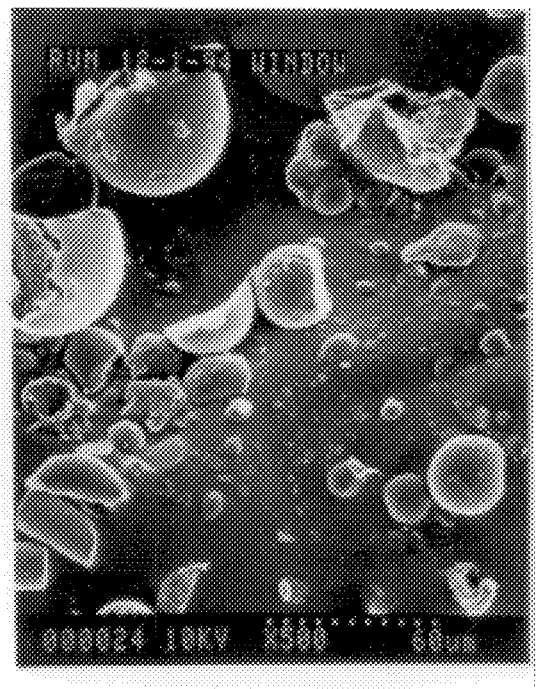
FIGS. 9a and 9b are a pair of SEM micrographs (500× and 1,000× magnification, respectively) of polylactic-glycolic acid polymer (RG503H) micronized by recrystallization from a 10 mg/ml ethyl acetate solution using the conventional SAS process with a 100 $\mu$m capillary nozzle.
Figure 9B:
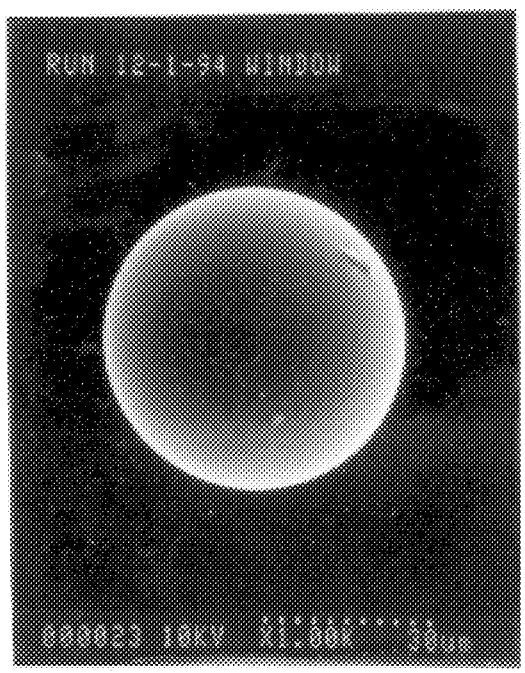

Pre-mixing of $CO_2$ with the DMSO solution prior to expansion, aimed at improving mass transfer efficiency, had little effect on particle size and morphology, but caused the formation of bubbles on the surface of the flakes. The formation of relatively large, agglomerated particles at increased polymer concentrations parallel those of Dixon, D. J., Johnston, K. P. and Bodmeier, R. A., 1993, Polymeric materials formed by precipitation with a compressed antisolvent. *Amer. Inst. Chem. Eng. J.* 39:127–139; Randolph et al.(1993); and Bodmeier, R., H. Wang, D. J. Dixon, S. Mawson, and K. P. Johnston, 1995, Polymeric microspheres prepared by spraying into compressed carbon dioxide. *Pharm. Res.* 12:1211–1217. As in the previous example, these results also demonstrate the increasing difficulty of atomization and particle micronization with increasing polymer concentration due to both an increase in solution viscosity and to premature mass transfer between the solution and $CO_2$. This observation is further corroborated in FIGS. 9a and 9b, which show that a reduction in the viscosity and/or surface tension of the solution through a change of solvent, i.e. from DMSO (1.9 cp and 41 dyn/cm) to ethyl acetate (0.46 cp and 24 dyn/cm) led to the formation of discrete microspheres (in FIGS. 9a and 9b, the sprayed solution is 10 mg/ml RG503H in ethyl acetate; P=1,500 psi; T=35° C.; $CO_2$ flow rate=5 ml/min.; solution flow rate=2.5 ml/min.; capillary I.D.=100 $\mu$m). The inability to attain sub-micron particles of average size smaller than 0.6 $\mu$m using the conventional SAS process is attributed to mass transfer limitations. These are overcome in the present invention as explained earlier and as demonstrated in the following example.

TABLE 2

Micronization of RG503H by Conventional SAS Recrystallization.
P = 1,500 psig; T = 35° C.; $CO_2$ flow rate = 5 ml/min.;
Solution Flow Rate = 2.5 ml/min.; Capillary
I.D. = 100 $\mu$m; Solvent is DMSO except for Run 6.

| Run # | Shape | Particle Size ($\mu$m) | [RG503H] (mg/ml) |
|---|---|---|---|
| 1 | whiskers | 15 | 0.5 |
| 2 | whiskers/flakes | 15/50 | 2.0 |
| 3 | whiskers/flakes | 25/>100 | 2.0 |
| 4 | flakes | 100 | 10.0 |
| 5 | amorphous | >500 | 100.0 |
| 6 | hollow microspheres | <50 | 10.0* |
| 7 | flakes with bubbles | >500 | 10.0^ |

*:Solvent is ethyl acetate.
^: Premixing of solvent and $CO_2$.

Figure 10:
FIG. 10 is an SEM micrograph (1,000× magnification) of RG503H micronized by recrystallization from a 10 mg/ml ethyl acetate solution using the nozzle of the present invention (compressed $CO_2$ is used as energizing gas and as antisolvent).

RG503H Particles Produced Using the Present Invention in which Compressed $CO_2$ is used as Energizing Gas and as Antisolvent FIG. 10 shows an SEM micrograph of RG503H particles recrystallized from a 10 mg/ml ethyl acetate solution. These particles are compared with particles shown in FIGS. 9a and 9b, which are obtained using the conventional SAS process. Both experiments were conducted at identical conditions of pressure, temperature, and solution flow rate (1,500 psig, 35° C., and 2.5 ml/min, respectively) within the crystallization chamber, except that the particles shown in FIG. 10 were obtained using the present invention in which compressed $CO_2$ was used as energizing gas. The $CO_2$ supply pressure was 1,600 psig. Similar to the particles seen in FIGS. 9a and 9b, the RG503H particles in FIG. 10 are also nearly spherical; however, the particles obtained using the present invention appear more discrete and are an order of magnitude smaller than particles in FIGS. 9a and 9b. As with the results obtained in the previous example, particle diameter is again narrowly distributed around 1 $\mu$m. Thus, the present invention produces smaller particles than the conventional process with less agglomeration, a property that is desirable, especially in the pharmaceutical industry.

EXAMPLE 3

Figure 11A:
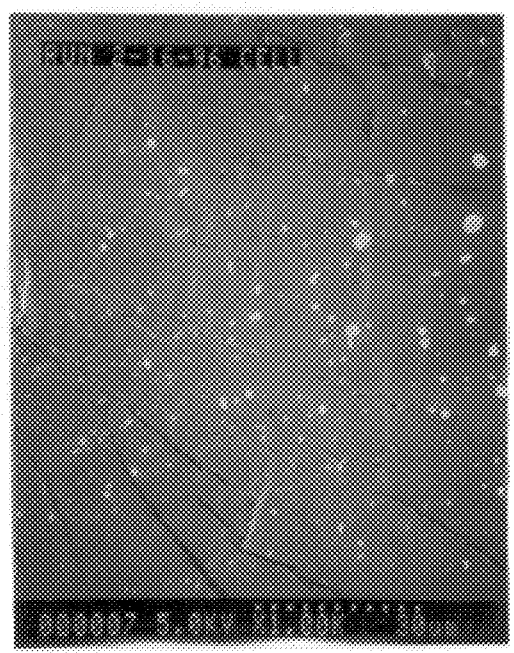
FIGS. 11a and 11b are a pair of SEM micrographs (1,000× and 10,000× magnification, respectively) of ibuprofen nanonized by recrystallization from a 30 mg/ml DMSO solution using the nozzle of the present invention (compressed $CO_2$ is used as energizing gas and as antisolvent).
Figure 11B:

Recrystallization of Ibuprofen from a DMSO Solution Using the Present Invention in which Compressed $CO_2$ Was Used as Energizing Gas and as Antisolvent FIGS. 11a and 11b show a pair of SEM micrographs of Ibuprofen particles recrystallized from a 30 mg/ml DMSO solution under the same operating conditions as in Example 2. Once again, particles appear to be discrete, particle sizes are small and, except for a fraction of micron-sized particles, most particles are smaller and in the range of 0.6 $\mu$m or less.

EXAMPLE 4

Recrystallization of Camptothecin from a DMSO Solution Using the Present Invention is which Compressed $CO_2$ Was used as Energizing Gas and as Antisolvent Camptothecin, as supplied by the vendor, appears as amorphous particles with diameters ranging from 1–10 $\mu$m.

Figure 12:
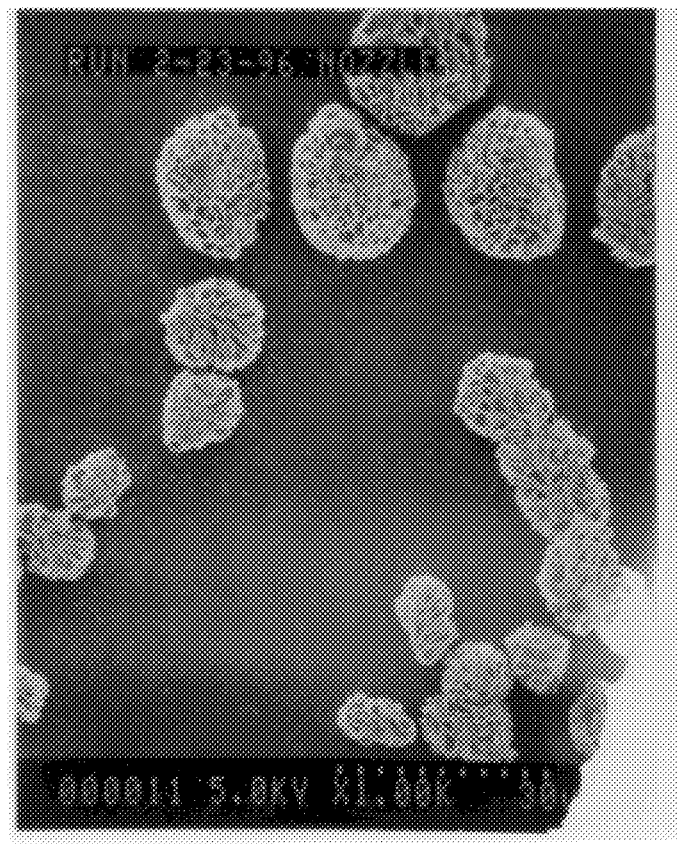
FIG. 12 is an SEM micrograph (1,000× magnification) of micronized camptothecin by recrystallization from a 5 mg/ml DMSO solution using the nozzle of the present invention (compressed $CO_2$ is used as energizing gas and as antisolvent).

FIG. 12 is an SEM micrograph of camptothecin particles recrystallized from a 5 mg/ml DMSO solution under the same operating conditions as in Example 2, (i.e., P=1,500 psig, 35° C. with a $CO_2$ back pressure of roughly 100 psig). Particles are nearly spherical and discrete. Although relatively large in size (5–20 µm), these particles appear to be porous. The relatively high surface area of these particles should increase their dissolution rate and bioavailability.

Figure 13A:
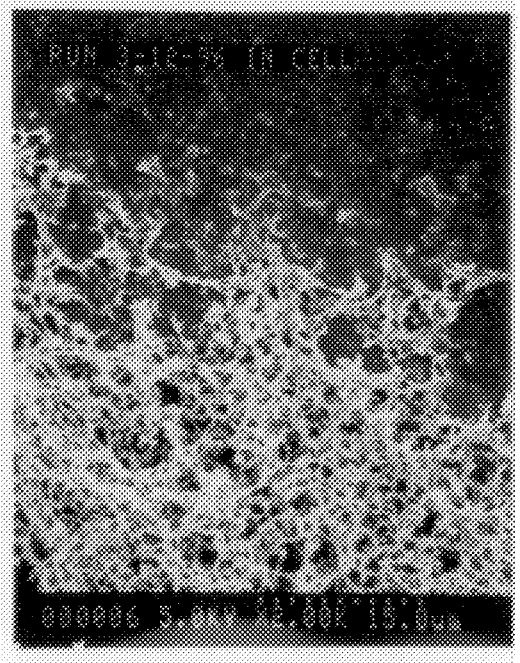
FIG. 13a and 13b are a pair of SEM micrographs (2,000× and 15,000× magnification, respectively) of camptothecin nanonized by recrystallization from a 5 mg/ml DMSO solution using the nozzle of the present invention (compressed $CO_2$ is used as energizing gas and as antisolvent)
Figure 13B:
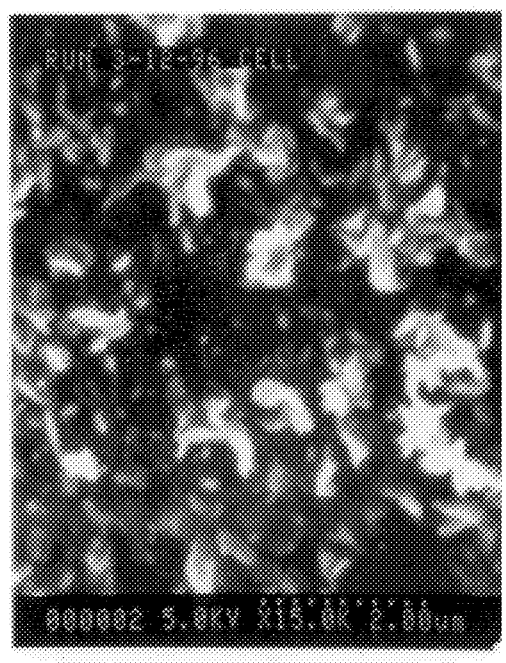

FIGS. 13a and 13b show a pair of SEM micrographs of camptothecin particles recrystallized from a 5 mg/ml DMSO solution under the same operating conditions as in Example 1, FIGS. 7 and 8 (i.e., P=1,250 psig, T=35° C., with a $CO_2$ back pressure of 600 psig). Because of the higher expansion and velocities of the compressed gas (from 1,850 psig to 1,250 psig compared to 1,600 psig to 1,500 psig in the previous experiment), smaller particles are formed. As seen in FIG. 13b, particles are non-agglomerated with the average diameter in the range of 0.5 µm. Here again, as in Example 1 where favorable operating conditions were used, nanoparticles were produced.

Alternative Embodiments

Note that in an alternative process, the chamber contains liquid $CO_2$ or other liquid antisolvent as opposed to supercritical $CO_2$ or another antisolvent in its supercritical form. In this case, the volume above the liquid phase (i.e., the vapor phase) contains mostly the light gas or the antisolvent which powers the nozzle of the present invention, and recrystallization takes place in either the liquid phase (when a light gas is used to power the spray nozzle) or in both phases (when an antisolvent is used to power the spray nozzle). In the case where the antisolvent itself is used to power the nozzle, operating conditions are such that the energizing gas at its near-critical or supercritical state will nearly attain the conditions in the recrystallization chamber upon expansion through the nozzle. This alternative process is attractive for applications where containment of the recrystallized particles in the crystallization chamber is difficult because of entrainment in the supercritical phase. The lower buoyancy of liquids compared to supercritical fluids can minimize losses of small micro-sized or nano-sized particles.

Other Applications For The Inventive Method And Apparatus Disclosed Herein

This invention finds application in areas where reduction in particle size to below 1 µm is desired for the purpose of increasing the surface area, the rate of dissolution, reactivity, or bioavailability.

The disclosed invention also finds application in areas where recrystallization of microparticles or nanoparticles from organic solutions is desirable. These applications can find use in the production of foods, electronic equipment, explosives, pharmaceutical products or intermediates (micronization, nanonization, coating, microencapsulation, lyophilization, and co-precipitation), catalysts (micronization and nanonization to increase the surface area of active sites or support), explosives (improved reactivity), coating (finer coatings), polymers (micronization and nanonization), pesticides (micronization, nanonization, and microencapsulation), and other chemicals (micronization, nanonization, and microencapsulation).

Antisolvents useful in the application of this invention include, but are not limited to, $CO_2$, propane, butane, isobutane, $CHF_3$, $SF_6$, and $N_2O$. Organic solvents may be either of the class of aromatic hydrocarbons, alcohols, esters, ethers, ketones, amines, or nitrated or chlorinated hydrocarbons. Preferred solvents include acetone, ethanol, methanol, dichloromethane, ethyl acetate and DMSO.

Conclusion

The method and apparatus of the present invention overcome the disadvantages associated with conventional SAS processes in several ways. The high-velocity wavefront and/or turbulence established at the exit of the nozzle by the energizing gas breaks up the solution exiting the nozzle into a fine spray of droplets. The mass transfer rate between the spray droplets and the surrounding antisolvent phases is essentially proportional to the surface area of the spray droplets, and the antisolvent and solute concentration gradients. Use of the nozzle of the present invention provides a means for enhancing mass transfer rates through an increase in both the surface area of the spray and the interphase concentration gradients.

One effect of the creation of the small size droplets is to increase the specific surface area of the droplets, that in turn increases the rate of mass transfer. Also, in contrast to the electrically energized nozzle which produces a relatively low velocity spray, the compressed energizing gas passes the atomized droplets as it enters the supercritical antisolvent at high velocity and thereby creates a turbulence which prevents a build-up of depleted solvent in the proximity of the atomized spray. An increase in the concentration gradients between the droplet phase and the antisolvent phase provides an increased driving force for interphase mass transfer.

Other advantages of the compressed gas-powered nozzle of the present invention over other nozzles in their use for recrystallization of solutes from organic solutions or suspensions are:

1. The relatively large size of the line through which the solution flows through the nozzle compared to either capillary or micro-orifice nozzles allows for higher solution throughput and reduces the probability of nozzle plugging.
2. The same fluid can be used for both energizing the spray nozzle as well as an anti-solvent.
3. The high velocity of the energizing gas stream imparts a high velocity to the spray droplets, and therefore reduces the tendency for droplet coalescence which can lead to the formation of larger particles.
4. The high velocity of the gas or supercritical fluid energizing stream provides a buffer zone at the tip of the nozzle that is either a gas or a low-density supercritical fluid. If the gas has little or no antisolvent power, the buffer zone at the tip of the nozzle serves to delay recrystallization until after secondary atomization of the spray has been achieved. This case is most attractive when using highly viscous or concentrated (nearly saturated or supersaturated) solutions.

If the energizing gas is itself a supercritical fluid antisolvent, the buffer zone is a highly turbulent zone of nearly pure antisolvent, thereby maximizing mass transfer rates between the droplets and the antisolvent while minimizing the droplet coalescence rate. This case is most attractive when recrystallizing drugs or polymers from solutions with low solute concentrations. Use of a compressed gas with intermediate antisolvent power (i.e. a mixture of light gas and antisolvent) provides a means for controlling interphase mass transfer rates, and therefore means for controlling particle size.

The teachings of all references cited herein and those cited in the Provisional Application Ser. No. 60/012,593 (identified above), and all references cited therein, are incorporated herein by reference.

Particle Coating

In Examples 5–8, coating of model core materials (1.5 mm nonpareil sugar beads and 2 mm glass beads) with either a drug (hydrocortisone) or a polymer (poly(D,L-lactide-glycolide, RG503H) was investigated. Hydrocortisone was acquired from Sigma Chemical Co., St. Louis, Mo. and was used with no further purification. The polymer was acquired from the Henley Co., Montvale, N.J. and contained a 1:1 molar ratio of lactide to glycolide and had an inherent viscosity in chloroform of 0.3 cps. RG503H is FDA approved for administration to humans, is non-toxic, non-tissue reactive, biogrades to non-toxic products, and is suited for surgical sutures.

Certified grade ethylacetate and DMSO (99.9% purity, Fisher Scientific, Fairlawn, N.J.), bone dry $CO_2$ (99.8% purity, Genex, Kansas City) were used with no further purification. Recrystallized microparticles were collected on glass beads or nonpareil sugar beads. Particles that deposit on the cell walls were also collected for analysis. Particle morphology and coating uniformity were evaluated by SEM (Hitachi, Model S-570). Particle size was also estimated by SEM. The SEM samples were sputter coated with Au/Pd alloy.

Figure 14:
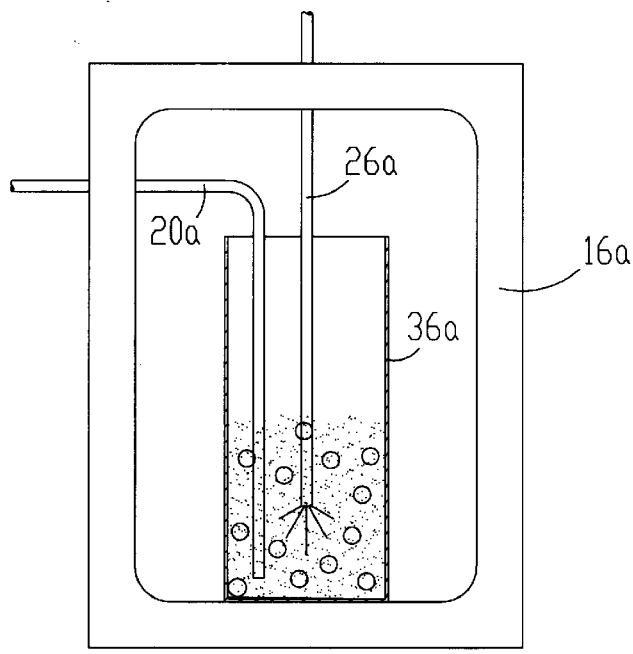
FIG. 14 is a schematic view of a modified precipitation vessel specifically adapted for the coating of core particles in the overall apparatus of FIG. 1.

FIG. 14 is a schematic view of a modified view cell used in the FIG. 1 apparatus in the coating experiments. Specifically, the FIG. 1 apparatus was employed except that the modified view cell 16a was used in lieu of the cell 16. The cell 16a in the experiments was equipped with an internal, 16 cm-long, 8 ml glass tube 36a in place of the rod 36 of FIG. 1, a $CO_2$ extension line 20a leading from port 20 to the bottom of tube 36a, and the capillary nozzle tubing 26a was extended downwardly to a point adjacent the open end of tube 36a.

In use, the 16-cm long, 8 ml glass tube 36a is first charged with nonpareil sugar beads or glass beads, and then fitted at the bottom of the view cell as shown in FIG. 14. When the bath temperature is stable at a desired value, $CO_2$ is pumped through the line 20a at a constant rate (typically 5 mL/min. of liquid $CO_2$) until pressure in the cell reaches a desired level (1500 psi). When temperature and pressure in the cell are stabilized, the organic solution (DMSO or ethyl acetate solution of drug and/or polymer) is metered through capillary nozzle tubing 26a. Both the organic mixture and $CO_2$ are preheated to operating temperature by passing through heat exchangers housed together with the cell in the adjacent water bath (see FIG. 1). In order to establish countercurrent flow and fluidize the beads, as described the $CO_2$ was introduced at the bottom of the tube through port line 20a while the organic solution of the coating material was sprayed from about 2 inches above. It is found that a minimum solution flow rate of 2.5 mL/min. is needed to consistently obtain a jet spray.

Fresh $CO_2$ and the organic solution streams thus mixed within the glass tube. Solution expansion caused the drug and/or polymer dissolved in the organic solvent to nucleate and the particles to crystallize and descend down the tube.

Recrystallized particles adhered either to the glass tube walls or deposited on the beads. Any particles escaping retention within the view cell chamber were retained on the steel frit housed in the T-shaped fitting at the central bottom port 38 (FIG. 1). A thermocouple inserted through this fitting was used to monitor the cell temperature. the drug/polymer depleted mixture of $CO_2$ and organic solution flowed through the step-motor controlled, heated micrometering valve assembly 40. Upon expansion to a subcritical pressure (typically close to atmosphere pressure), the mixture separates into an organic liquid phase and a $CO_2$ gas phase. Phase separation took place in flash drum 42; the organic solution flowed through the micrometering valve 44 and was collected in vessel 46. The solution was then analyzed for drug and polymer content. $CO_2$ was vented through a second micrometering valve 48, rotameter 59 and an electronic mass flowmeter 50 (all as shown in FIG. 1).

After the flow of organic solution was stopped, $CO_2$ flow was continued for another 1½ hours in order to flush out any organic solvent left in the cell, and to dry the collected particles. It was found that flowing $CO_2$ at 1500 psig for 1½ hours (roughly seven times the view cell volume) was adequate for flushing out the organic solvent present in the cell and for drying the particles. It was observed that no recrystallized particles could be recovered when the drying periods were shorter than one hour; in this case, particles adhering to the tube walls redissolved in the organic solvent during pressure reduction as the organic solvent condensed out of the $CO_2$ phase. Clearly an increase in $CO_2$ flow rate will reduce the required drying time; the $CO_2$ flow rate can also be set high enough so that the coating process can operate continuously while keeping the steady state concentration of solvent in the coating chamber at a low enough level that the mixture is always supercritical and no solvent condensation in the coating chamber takes place.

Following the drying period, the pressure was decreased to atmospheric level at a rate of −50 psi/min. The coated beads were discharged from the glass tube and analyzed by scanning electron microscopy (SEM).

Equipment and Experimental Procedures for Examples 5–8

EXAMPLE 5

Coating of Nonpareil Sugar Beads and Glass Beads with RG503H

Nonpareil sugar beads and glass beads 1.5 mm and 2 mm diameter respectively were first charged into a 16-cm long, 8 mL glass tube. The tube was then fitted at the bottom of the view cell (FIG. 14) and the cell was brought up to operating pressure with $CO_2$. A 10 mg/ml ethyl acetate solution of RG503H was them pumped into the glass tube for 5 minutes. In order to establish countercurrent flow and fluidize the beads, $CO_2$ was introduced at the bottom of the tube while the suspension was introduced from about 2 inches above. Capillary nozzle I.D., temperature, pressure, solution flow rate and $CO_2$ rate were 100 $\mu$m, 35° C., 1500 psig, 2.5 cc/min. and 5 mL/min. of chilled liquid $CO_2$ respectively.

Figure 15:
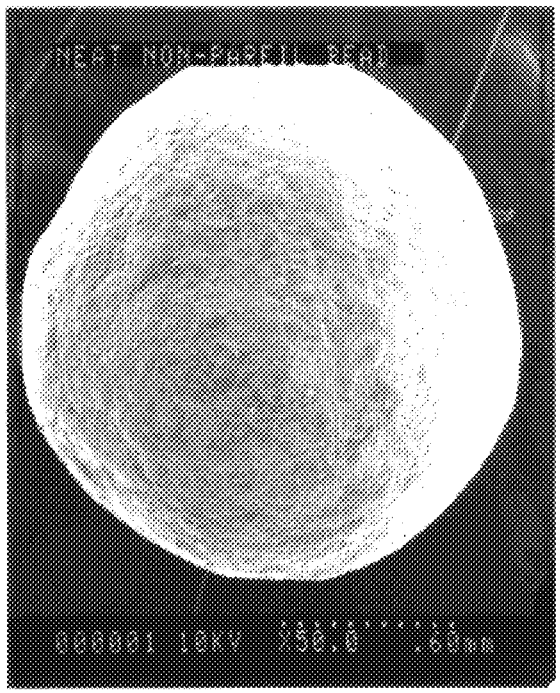
FIG. 15 is an SEM photograph of an uncoated nonpareil sugar bead used in Example 5.
Figure 16:
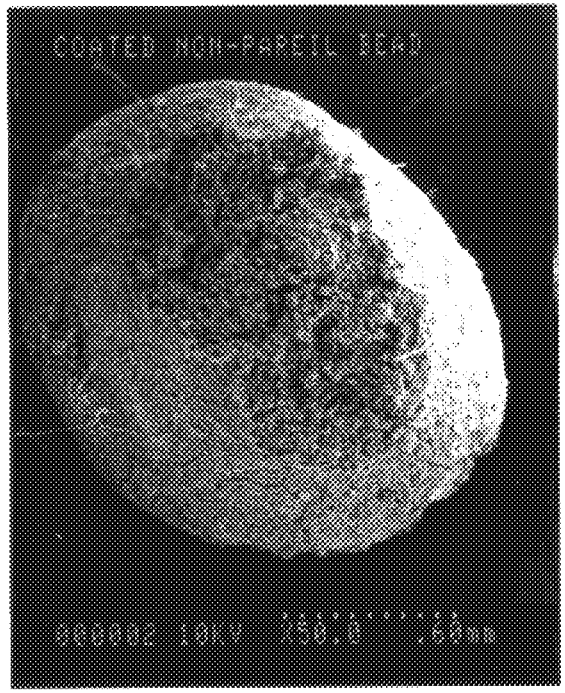
FIG. 16 is a SEM photograph of a final RG503H-coated nonpareil sugar bead.
Figure 17:
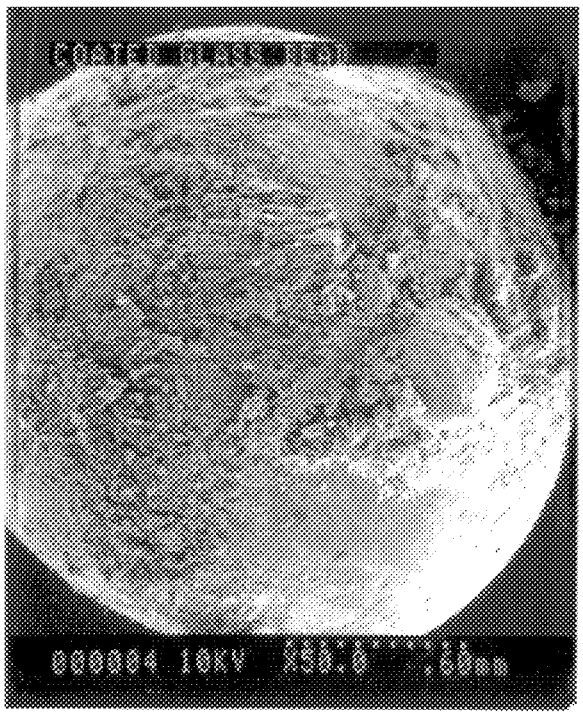
FIG. 17 is a SEM photograph of a RG503H-coated glass bead.
Figure 18:
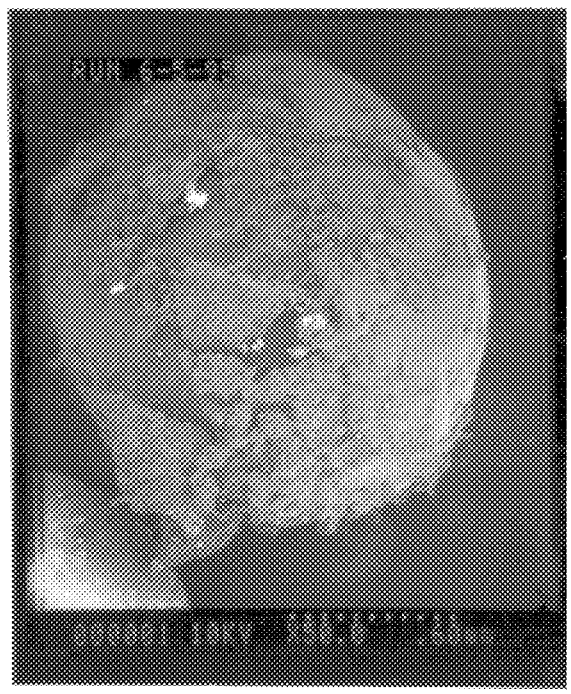
FIG. 18 is a SEM photograph of a RG503H-coated nonpareil sugar bead produced in accordance with Example 7.
Figure 19:
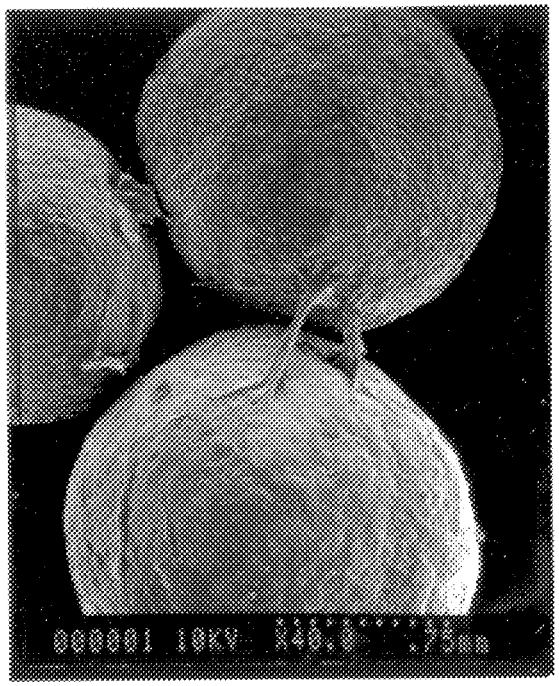
FIG. 19 is a SEM photograph of a RG503H-coated nonpareil sugar bead produced in accordance with Example 7.
Figure 20:
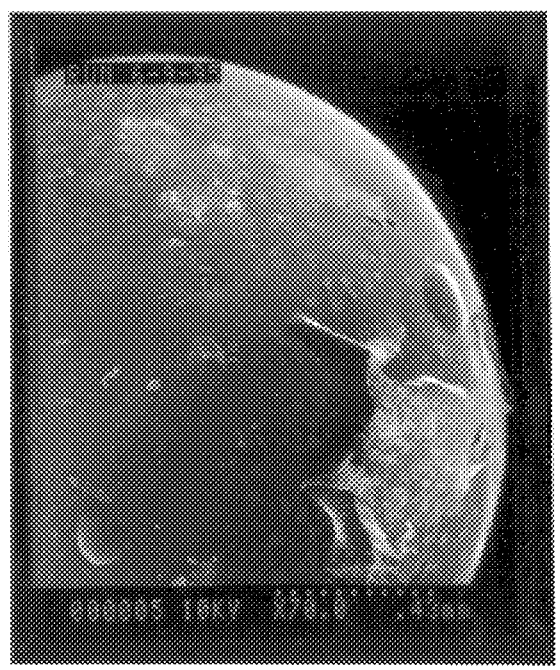
FIG. 20 is a SEM photograph of a hydrocortisone-coated glass bead produced in accordance with Example 8.

FIG. 15 is a micrograph of an uncoated nonpareil bead. FIGS. 16 and 17 show micrographs of a resulting coated nonpareil bead and glass bead respectively. The nonpareil bead is nearly uniformly coated with a layer of mostly microspheres of RG503H. Coating on the glass bead is less uniform possibly due to its larger size which reduces its mobility within the glass tube. The recrystallized microspheres (FIG. 16) are of similar size (roughly 10 $\mu$m) to those obtained in runs at identical conditions with the same solution in the absence of the beads (see Table 1).

In this experiment, constraining of the expansion to within the glass tube and reduction of the efficiency of the atomization process by virtue of pumping the solution into the relatively small volume glass tube caused the solution to expand as a pseudo-liquid phase rather than as microdroplets. The recrystallized polymer microparticles were thus not entrained in the SCF, and were able to coat the beads. As evidence of this observation is the fact that upon removal of the glass tube from the view cell, only the bottom half of the tube visibly contained polymer particles. The upper half, which was not reached by the solution upon expansion appeared polymer-free.

Operation under conditions of higher $CO_2$ flow rates (25 cc/min. as liquid) to improve the efficacy of the atomization step did eliminate the formation of the expanded liquid phase, but little coating was deposited on the beads due to entrainment of the recrystallized polymer microparticles by the high velocity SCF into the view cell, outside the glass tube, thereby reducing their probability of contacting the beads. Microparticle entrainment away from the region where the core material is confined can be avoided by eliminating the use of the glass tube and loading the core particles into the entire view cell. Alternatively, use of a modified cell approximating a Wurster coater would provide adequate conditions for antisolvent, solution or suspension, and substrate distribution within the coating chamber.

EXAMPLE 6

Concentration Effects on Coating of Nonpareil Sugar Beads with RG503H

In this study, a solution of 25 mg/ml of RG503H in ethyl acetate was recrystallized under the same conditions as in Example 6. FIG. 18 is an SEM micrograph of a coated nonpareil bead. Coating is less uniform than on beads coated as described in Example 5 using a 10 mg/ml ethyl acetate solution of RG503H. The increase in concentration appears to increase the size of the recrystallized particles and reduce the uniformity of the coating. The increase in recrystallized microparticle size was also observed in the absence of the beads.

EXAMPLE 7

Temperature Effects on Coating of Nonpareil Sugar Beads with RG503H

FIG. 19 shows an SEM micrograph of nonpareil sugar beads coated with RG503H recrystallized under the same conditions as in Example 6 except than the view cell temperature was held at 40° C. Under these conditions, the polymer is seen to deposit on the sugar beads as a continuous film. Thus, a small increase in temperature (from 35° C. to 40° C.) can be sufficient to change the texture of the coating layer. Agglomeration of the beads can be avoided by improving the conditions under which the fluidization is carried out. Alternatively, use of a modified cell approximating a Wurster coater would provide adequate conditions for antisolvent, solution or suspension, and substrate distribution within the coating chamber.

EXAMPLE 8

Coating of glass Beads with Hydrocortisone

FIG. 20 shows a micrograph of a glass bead collected from a run where a suspension of hydrocortisone in ethyl acetate was sprayed into $CO_2$ using the capillary nozzle. This suspension was prepared by filtering a 10 mg/mL suspension of hydrocortisone in ethyl acetate filtered through a 2 $\mu$m porosity paper. The 16-cm long, 8 ml glass tube was first charged with 1 gram of roughly 2 mm diameter glass beads, and then fitted at the bottom of the view cell. Operating temperature, pressure, solution flow rate and $CO_2$ flow rate were 35° C., 1500 psig, 2.5 mL/min. of liquid $CO_2$ respectively. The suspension was pumped for five minutes. As illustrated in FIG. 20, the beads can be nearly uniformly coated with a thin film of hydrocortisone. Formation of a film, as opposed to microparticles was expected as our studies and those of previously referenced investigators indicate that an increase in organic solution saturation level or concentration leads to the formation of amorphous particles with agglomerate to form films and porous structures.

Alternative Embodiments

Because of its environmentally benign nature compared to alternative organic solvent-based coating process, and its greater potential to form thin film coatings, the present coating process provides an attractive alternative to the powder coating electrostatic spraying technique. The instant process also provides an alternative to the Wurster coater technique. Alternatively, the core materials may be tumbled down a conveyor belt disposed in a high pressure $CO_2$ chamber while a solution or suspension is continuously sprayed on the core materials. Another alternative is to use this process for coating larger objects than drug tablets or pesticide granules. Because recrystallization can occur almost as soon as the spray exits the nozzle in the SAS process, a technique can be employed whereby a nozzle scans the surface of the object, and microparticles are rapidly deposited on the surface upon which the nozzle is spraying the solution. This process could be particularly useful for efficiently painting large surfaces. Another alternative is to coat a large object by merely expanding the solution spray onto a chamber containing the object without necessarily scanning the surface of the object.

Alternatively, adhesives or plasticizers can be added to the organic solution to facilitate adherence of the recrystallized particles to the surface of the substrate or to improve on the physical properties of the coating. Excipients such as colorants may also be added to the organic solution to enhance the aesthetic or functional properties of the coating.

Other Applications for the Coating Method and Apparatus

This invention finds application in all areas where particle coating by recrystallization of the shell material from an organic phase is desirable. These applications can find use, but are not limited to, in coating of: pharmaceutical tablets, granules, pellets or capsules; pesticides; fertilizers; catalysts; seeds; salts; circuit boards; wires, containers and lids.

Antisolvents useful in the application of this invention include, but are not limited to, $CO_2$, propane, butane, isobutane, $CHF_3$, $SF_6$ and $N_2O$. Organic solvents may be either of the class of aromatic hydrocarbons, alcohols, esters, ethers, ketones, amines, or nitrated or chlorinated hydrocarbons. Preferred solvents include acetone, methanol, ethanol, propanol, isopropanol, dichloromethane, ethyl acetate and DMSO. Blends of these solvents may also be used.

Coating materials useful for this application include sugars, polymers such as poly-lactide glycolide copolymers (PLGA), PLA, PGA, polyvinylpyrrolidone, polyethylene glycols and methacrylic acid ester. The largest group of film forming resins are the cellulose ethers, especially the hydroxypropylmethyl cellulose. Other cellulose ethers include hydroxypropyl cellulose, methyl hydroxypropyl cellulose, methyl cellulose and ethyl cellulose.

Plasticizers may also be added to the coating solution or suspension if properties of the polymeric coating are not adequate. These plasticizers are used to modify the properties of the coating material through a reduction in its glass transition temperature. This can result in a less brittle, softer and more mechanical-stress resistant coating. Plasticizers can also decrease the permeability of the film to moisture and enhance the stability of the product. Common plasticizers include, but are not limited to, phthalate esters, castor oils, acetylated monoglycerides, triacetin, glycerin, propyleneglycol, and polyethylene glycols.

Colorants such as dyes and pigments including iron oxides and titanium dioxide, may also be added to enhance the aesthetic appeal or the physical properties of the coating.

Lyophobic Precipitation

In Examples 9–12, the lyophobic precipitation of drugs (hydrocortisone, phenytoin, ibuprofen) in containers was investigated. Hydrocortisone, phenytoin and ibuprofen were acquired from Sigma Chemical Co., St. Louis, Mo. and were used without further purification. Certified grade acetone, DMSO (99.9% purity, Fisher Scientific, Fairlawn, N.J.) and bone dry $CO_2$ (99.8% purity, Air Products, Lenexa) were used.

Figure 21:
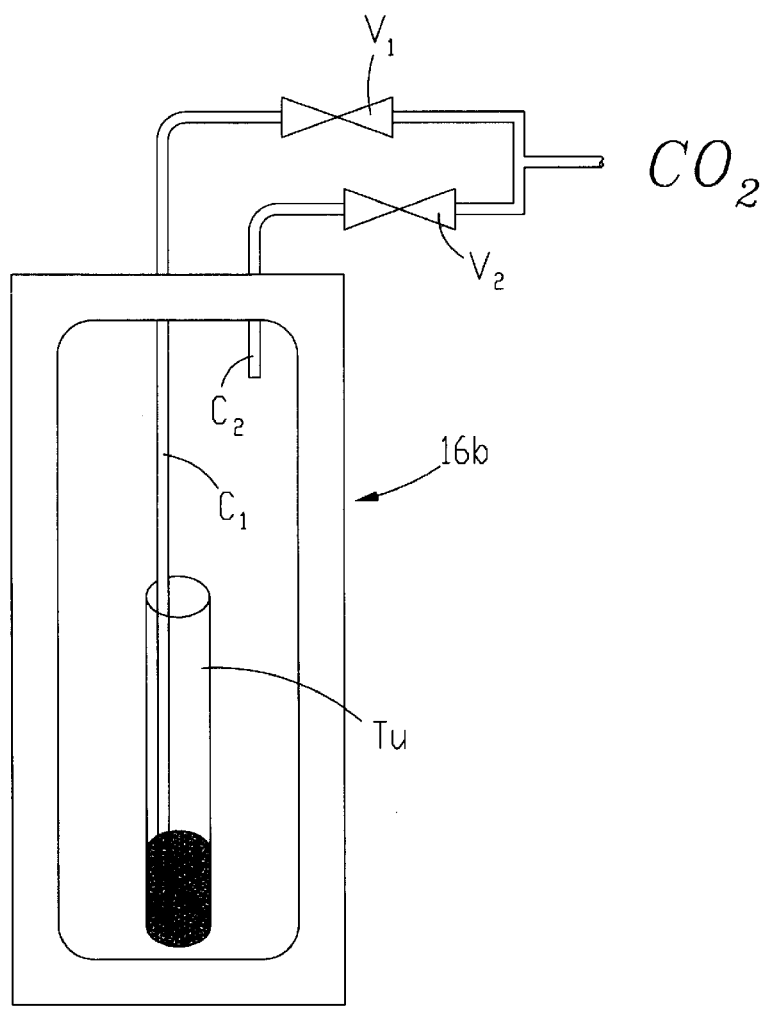
FIG. 21 is a schematic representation of apparatus useful in the lyophobic precipitation aspects of the present invention.

The FIG. 1 apparatus was employed in Example 9 except the modified view cell 16 was fitted with a 15 cm long glass tube sealed on one end with a 4 $\mu$m frit. The tube mimicked a specialized use container for the purposes of these experiments. For examples 10, 11 and 12 the FIG. 1 apparatus was employed except that view cell 16 was replaced by 95 mL view cell 16b of FIG. 21. The cell 16b was equipped with two carbon dioxide input lines $C_1$ and $C_2$, each having a corresponding valve $V_1$ and $V_2$ interposed therein; the valves were in turn coupled to a common source of $CO_2$ as shown in FIG. 21. The view cell 16b was also equipped in these examples with 12×75 mm borosilicate tubes $T_u$ which mimicked final use containers. As illustrated in FIG. 21, the $CO_2$ line $C_1$ extended downwardly into the interior of the tube $T_u$ beneath the level of liquid therein.

EXAMPLE 9

Batch precipitation of hydrocortisone from a 200 mg/ml DMSO solution was undertaken. A 1 cc aliquot of solution was pumped into the fritted glass tube positioned inside view cell 16. Pressure and temperature were maintained at 1,575 psig and 31° C.

Twelve standard liters of $CO_2$ were introduced from the bottom end of the tube and through the frit to expand the solvent and recrystallize the drug. Following this expansion period, 300 standard liters of $CO_2$ were introduced from the top end of the glass tube to "push" the expanded solution out of the tube through the glass frit and to dry the particles for one hour. This method is attractive because it provides a means for rapidly expanding the solution and recrystallizing the drug, while preventing the solution to expand over the upper rim of the glass tube (or dispensing container).

EXAMPLE 10

1 mL of a 24.1 mg/mL solution of phenytoin in acetone was transferred into the borosilicate tube. The tube was placed in view cell 16b of FIG. 21. The line $C_1$ extended through the phenytoin solution to the bottom of the borosilicate tube $T_u$. The cell was quickly pressurized to 800 psig with $CO_2$ at 40° C. through line $C_2$. It is noted that the $CO_2$ introduction rate via line $C_1$ must be sufficiently slow to prevent the forceful ejection of solution. Therefore, initial pressurization can be conducted more quickly using line $C_2$.

Following initial pressurization, the valve $V_2$ is closed and $CO_2$ was introduced through line $C_1$ at 20 g/min for 9 minutes. The solution expanded and the drug was observed to precipitate. When the expanded solution reached the top of the borosilicate tube the $CO_2$ flow rate in line $C_1$ was decreased to 4.5 g/min to minimize drug loss as the expanding solvent overflowed the top of the test tube. After 8 minutes, the pressure within cell 16b reached 1,300 psig. Total $CO_2$ introduction via bubbling through line $C_1$ was 200 g. The cell was then depressurized and the borosilicate tube containing product was retrieved.

Figure 22A:
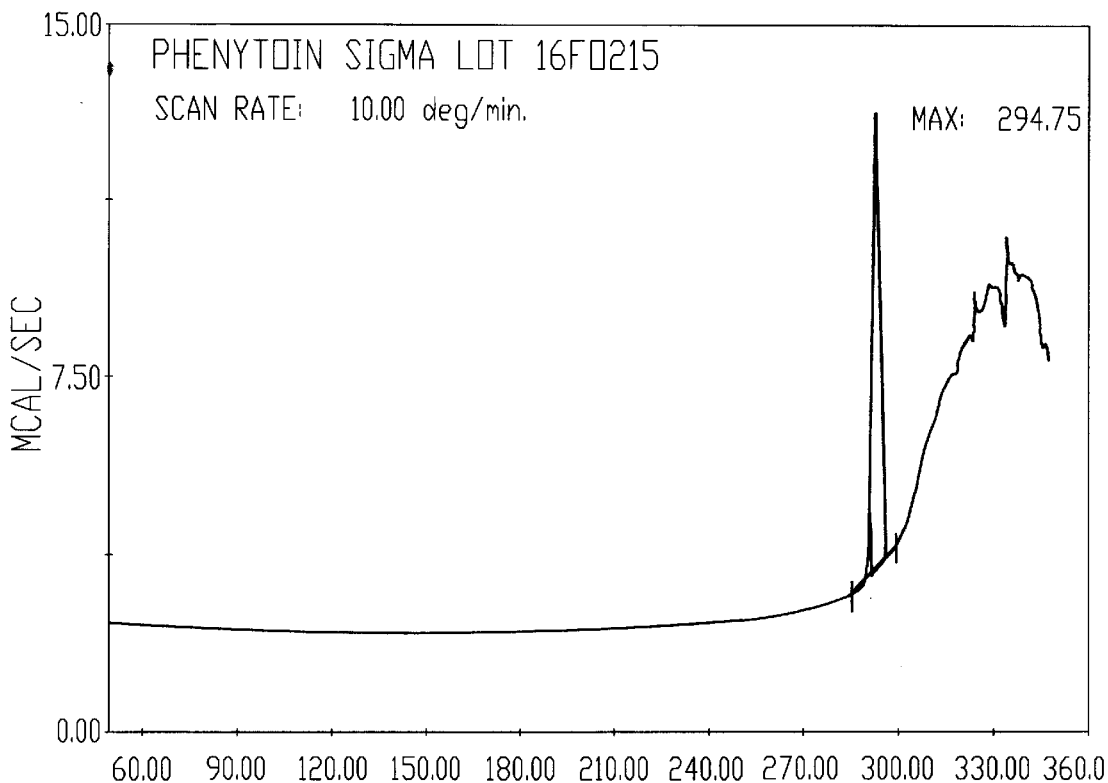
FIG. 22a is a differential scanning calorimetry thermogram of unprocessed phenytoin.
Figure 22B:
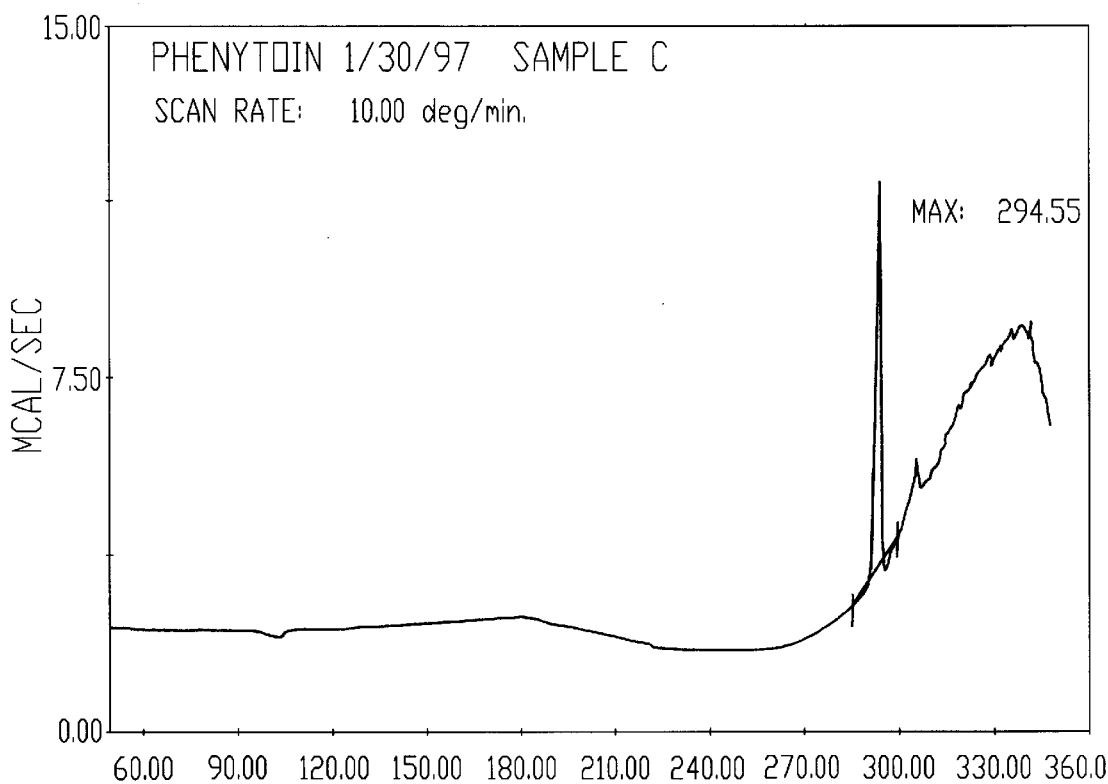
FIG. 22b is a differential scanning calorimetry thermogram of phenytoin processed by lyophobic precipitation in accordance with Example 10.

The precipitated phenytoin (FIG. 22b) was compared to the starting material (FIG. 22a) by Differential Scanning Calorimetry (DSC) and found to exhibit enthalpic transitions consistent with the starting material.

EXAMPLE 11

1 mL of a 30 mg/mL solution of ibuprofen in DMSO was transferred into the borosilicate tube. The tube was placed in the view cell 16b of FIG. 21. Line $C_1$ extended through the ibuprofen solution to the bottom of the borosilicate tube. The cell was quickly pressurized to 620 psig with $CO_2$ at 40° C. through line $C_2$. The valve $V_2$ on line $C_2$ was closed and $CO_2$ was then introduced through line C at flow rates ranging between 9 and 36 g/min.

The solution expanded and the drug was observed to precipitate. When the expanded solution reached the top of the borosilicate tube the $CO_2$ flow rate in line $C_1$ was decreased to 0.9 g/min for minute 12 minutes. No solvent was observed to remain in the test tube. Precipitate was observed on the tube walls. This was a total $CO_2$ introduction via bubbling through line $C_1$ of 125 g. Flow was then increased in line $C_1$ to 18 g/min for 1.5 minutes. The cell was depressurized and the tube containing product was retrieved.

EXAMPLE 12

1 mL of a 12.6 mg/mL solution of phenytoin in acetone was transferred into the borosilicate tube $T_u$. The tube was placed in view cell of FIG. 21. The view cell 16b was placed in a solid state ultrasonic bath (Fisher Scientific). The cell was quickly pressurized to 900 psig with $CO_2$ at 40° C. through line $C_2$. The ultrasonic bath was energized to produce ultrasonic energy at 43 kHz. After one hour, the solution had expanded to three times its initial volume and the drug was observed to precipitate. Upon depressurization, the precipitated drug redissolved in the acetone. Continued processing as described or direct sonication of the drug solution container would ultimately result in the isolation of solid drug.

We claim:

1. A process for the precipitation of small particles comprising the steps of:
    providing a fluid dispersion including a continuous phase dispersant with at least one substance to be precipitated dispersed in the dispersant; and
    contacting said dispersion with an antisolvent in a precipitation zone at near- or supercritical conditions for the antisolvent, and causing said substance to precipitate and form small particles,
    said antisolvent being miscible with said dispersant, said substance being substantially insoluble in the antisolvent,
    said contacting step comprising the steps of
        passing said fluid dispersion through a first passageway and first passageway outlet into said precipitation zone containing said antisolvent;
        passing an energizing gas stream along a second passageway and through a second passageway outlet proximal to the first outlet, said passage of said energizing gas stream through said second outlet generating high frequency sonic waves of said energizing gas adjacent said first passageway outlet for breaking up said fluid dispersion into extremely small droplets; and causing said antisolvent within said precipitation zone to deplete said dispersant and precipitate small particles of said substance.

2. The process of claim 1, said dispersion being a solution, said dispersant being a solvent and said substance being a solute dissolved in said solvent.

3. The process of claim 1, said conditions during said contacting step being from about 0.7–1.4 $T_c$ and from about 0.2–7 $P_c$ of said antisolvent.

4. The process of claim 3, said conditions being from about 1–1.2 $T_c$ and from about 0.9–2 $P_c$ of said antisolvent.

5. The process of claim 1, said dispersant and antisolvent being essentially completely miscible in all proportions thereof.

6. The process of claim 1, said dispersant comprising at least about 50% by weight of said dispersion.

7. The process of claim 6, said dispersant comprising at least about 90% by weight of said dispersion.

8. The process of claim 1, said energizing gas being the same as said antisolvent.

9. The process of claim 1, said antisolvent being selected from the group consisting of carbon dioxide, propane, butane, isobutane, nitrous oxide, sulfur hexafluoride and trifluoromethane.

10. The process of claim 1, said second passageway presenting a converging section and a corresponding restricted throat, with a diverging section downstream from said throat and leading to said second outlet.

11. The process of claim 10, said first passageway being coaxially disposed within said second passageway, with said first passageway outlet downstream of said restricted throat.

12. The process of claim 10, including an annular resonator cavity disposed adjacent and in communication with said diverging section.

13. The process of claim 1, including the step of generating high frequency waves of said energizing gas at a frequency of at least about 0.5 kHz.

14. The process of claim 13, said frequency being from about 10–100 kHz.

15. The process of claim 1, including the step of causing said dispersant depletion and particle precipitation so as to obtain particles having an average diameter of from about 0.1–10 $\mu$m.

16. The process of claim 15, said average diameter being up to about 0.6 $\mu$m.

17. The process of claim 1, said energizing gas stream having an inherent level of kinetic energy, a substantial portion of said energizing stream kinetic energy being converted to acoustic energy by virtue of said passage of said energizing gas stream through said second outlet.

18. The process of claim 17, at least about 1% of said inherent kinetic energy being converted to acoustic energy.

19. The process of claim 1, said energizing gas being selected from the group consisting of air, oxygen, nitrogen, helium, carbon dioxide, propane, butane, isobutane, trifluoromethane, nitrous oxide, sulfur hexafluoride and mixtures thereof.

20. The process of claim 1, said substance being a medicament.

21. A process for coating of core particles with a desired substance, said process comprising the steps of:

spraying a fluid dispersion into an enclosed precipitation zone containing a quantity of antisolvent at near-or supercritical conditions for the antisolvent, said fluid dispersion including a continuous phase dispersant with said desired substance dispersed therein, said antisolvent being miscible with said dispersant and said substance being substantially insoluble in the antisolvent;

creating a turbulent fluidized flow of said core particles within said precipitation zone by placing a quantity of said core particles within said precipitation zone and passing a fluidizing gas stream comprising said antisolvent into the precipitation zone; and causing said antisolvent to deplete said dispersant and precipitate said substance onto said fluidized core particles.

22. The process of claim 21, said dispersion being a solution, said dispersant being a solvent and said substance being a solute dissolved in said solvent.

23. The process of claim 21, said conditions during said contacting step being from about 0.7–1.4 $T_c$ and from about 0.2–7 $P_c$ of said antisolvent.

24. The process of claim 23, said conditions being from about 1–1.2 $T_c$ and from about 0.9–2 $P_c$ of said antisolvent.

25. The process of claim 21, said dispersant and antisolvent being essentially completely miscible in all proportions thereof.

26. The process of claim 21, said dispersant comprising at least about 50% by weight of said dispersion.

27. The process of claim 26, said dispersant comprising at least about 90% by weight of said dispersion.

28. The process of claim 21, said fluidizing gas being the same as said antisolvent.

29. The process of claim 21, said antisolvent being selected from the group consisting of carbon dioxide, propane, butane, isobutane, nitrous oxide, sulfur hexafluoride and trifluoromethane.

30. The process of claim 21, said spraying step comprising the steps of passing said fluid dispersion through a first passageway and first passageway outlet into said precipitation zone, and passing an energizing gas stream along a second passageway and through a second passageway outlet proximal to the first outlet, said passage of said energizing gas stream through said second outlet generating high frequency waves of said energizing gas adjacent said first passageway outlet for breaking up said fluid dispersion into extremely small droplets.

31. The process of claim 30, said second passageway presenting a converging section and a corresponding restricted throat, with a diverging section downstream from said throat and leading to said second outlet.

32. The process of claim 31, said first passageway being coaxial disposed within said second passageway, with said first passageway outlet downstream of said restricted throat.

33. The process of claim 31, including an annular resonator cavity disposed adjacent and in communication with said diverging section.

34. The process of claim 30, including the step of generating high frequency waves of said energizing gas at a frequency of at least about 0.5 kHz.

35. The process of claim 34, said frequency being from about 10–100 kHz.

36. The process of claim 21, including the step of causing said dispersant depletion and particle precipitation so as to obtain particles having an average diameter of from about 0.1–10 $\mu$m.

37. The process of claim 36, said average diameter being up to about 0.6 $\mu$m.

38. The process of claim 30, said energizing gas stream having an inherent level of kinetic energy, a substantial portion of said energizing stream kinetic energy being converted to acoustic energy by virtue of said passage of said energizing gas stream through said second outlet.

39. The process of claim 38, at least about 1% of said inherent kinetic energy being converted to acoustic energy.

40. The process of claim 30, said energizing gas being selected from the group consisting of air, oxygen, nitrogen, helium, carbon dioxide, propane, butane, isobutane, trifluoromethane, nitrous oxide, sulfur hexafluoride and mixtures thereof.

41. The process of claim 21, said fluidizing gas stream having a concentration of said antisolvent therein of at least about 50% by weight.

42. The process of claim 41, said fluidizing gas stream consisting essentially of said antisolvent.

43. The process of claim 21, said substance being a medicament.

44. The process of claim 21, said core particles having a maximum dimension of up to about 15 mm.

45. The process of claim 44, said maximum dimension being up to about 1 mm.

46. The process of claim 21, said core particles being selected from the group consisting of beads of sugar and glass.

47. A process for preparing and administering to a patient a medicament, comprising the steps of:

providing a use container for said medicament;

contacting within said use container a fluid dispersion including a dispersant with said medicament dispersed therein, and an antisolvent at near- or supercritical conditions for the antisolvent, and causing said antisolvent to precipitate medicament from the dispersion as small particles;

removing said antisolvent from said use container and sealing the use container with said medicament particles therein; and withdrawing at least one dose of said medicament from said use container and administering the dose to said patient.

48. The process of claim 47, said withdrawing step comprising the steps of forming a liquid injectable dosage form by adding an injectable carrier to said medicament to form a mixture within said use container, and withdrawing a dosage of said mixture.

49. The process of claim 47, said contacting step comprising the steps of placing said dispersions within said use container and passing said antisolvent therethrough.

50. The process of claim 47, said dispersion being a solution, said dispersant being a solvent and said medicament being a solute dissolved in said solvent.

51. The process of claim 47, said conditions during said contacting step being from about $0.7$–$1.4$ $T_c$ and from about $0.2$–$7$ $P_c$ of said antisolvent.

52. The process of claim 51, said conditions being from about $1$–$1.2$ $T_c$ and from about $0.9$–$2$ $P_c$ of said antisolvent.

53. The process of claim 47, said dispersant and antisolvent being essentially completely miscible in all proportions thereof.

54. The process of claim 47, said dispersant comprising at least about 50% by weight of said dispersion.

55. The process of claim 54, said dispersant comprising at least about 90% by weight of said dispersion.

56. The process of claim 47, said antisolvent being selected from the group consisting of carbon dioxide, propane, butane, isobutane, nitrous oxide, sulfur hexafluoride and trifluoromethane.

57. The process of claim 47, including the step of causing said dispersant depletion and particle precipitation so as to obtain particles having an average diameter of from about $0.1$–$10$ $\mu$m.

* * * * *